(12) United States Patent
Bjornson et al.

(10) Patent No.: US 8,815,858 B2
(45) Date of Patent: Aug. 26, 2014

(54) HETEROCYCLIC FLAVIVIRIDAE VIRUS INHIBITORS

(75) Inventors: Kyla Bjornson, San Mateo, CA (US); Steven S. Bondy, Danville, CA (US); You-chul Choi, Foster City, CA (US); Chien-Hung Chou, Livermore, CA (US); Ruchika Mishra, San Jose, CA (US); James D. Trenkle, Oakland, CA (US); Winston C. Tse, Redwood City, CA (US); Randall W. Vivian, San Mateo, CA (US); James G. Taylor, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 13/699,142

(22) PCT Filed: May 20, 2011

(86) PCT No.: PCT/US2011/037305
§ 371 (c)(1),
(2), (4) Date: Mar. 6, 2013

(87) PCT Pub. No.: WO2011/146817
PCT Pub. Date: Nov. 24, 2011

(65) Prior Publication Data
US 2013/0171102 A1    Jul. 4, 2013

Related U.S. Application Data

(60) Provisional application No. 61/347,215, filed on May 21, 2010.

(51) Int. Cl.
| | | |
|---|---|---|
| *A61K 31/50* | (2006.01) | |
| *A61K 31/497* | (2006.01) | |
| *A61K 31/519* | (2006.01) | |
| *A61K 38/21* | (2006.01) | |
| *C07D 487/00* | (2006.01) | |
| *C07D 409/00* | (2006.01) | |

(52) U.S. Cl.
USPC ............ 514/248; 514/252.02; 514/265.1; 424/85.4; 544/236; 544/238; 544/280

(58) Field of Classification Search
USPC .......... 514/248, 252.02, 265.1; 424/85.4; 544/236, 238, 280
See application file for complete search history.

(56) References Cited

U.S. PATENT DOCUMENTS

| | | | |
|---|---|---|---|
| 4,996,206 A | 2/1991 | Taylor et al. | |
| 5,248,775 A | 9/1993 | Taylor et al. | |
| 5,726,302 A * | 3/1998 | Ugarkar et al. | 536/27.13 |
| 7,648,998 B2 | 1/2010 | Bondy et al. | |
| 8,232,278 B2 | 7/2012 | De Jonghe et al. | |
| 8,338,435 B2 | 12/2012 | Herdewijn et al. | |
| 2006/0052602 A1 | 3/2006 | Kim et al. | |
| 2006/0252791 A1 | 11/2006 | Bondy et al. | |
| 2007/0724418 * | 10/2007 | Leuven et al. | 514/300 |
| 2008/0182870 A1 | 7/2008 | Bondy et al. | |
| 2008/0207678 A1* | 8/2008 | Bondy et al. | 514/300 |
| 2009/0226398 A1* | 9/2009 | Leivers et al. | 424/85.4 |
| 2009/0285782 A1 | 11/2009 | Gao et al. | |
| 2010/0143299 A1 | 6/2010 | Gao et al. | |
| 2010/0305117 A1 | 12/2010 | Herdewijn et al. | |

FOREIGN PATENT DOCUMENTS

| | | |
|---|---|---|
| WO | WO-2004/005286 A2 | 1/2004 |
| WO | WO-2005/063744 A2 | 7/2005 |
| WO | WO-2006/033703 A1 | 3/2006 |
| WO | WO-2008/005519 A2 | 1/2008 |
| WO | WO-2008/133669 A2 | 11/2008 |
| WO | WO-2009/009001 A1 | 1/2009 |
| WO | WO-2009/111501 A1 | 9/2009 |

OTHER PUBLICATIONS

Boyer et al., "Pathogenesis, diagnosis and management of hepatitis C," J Hepatol. 32(1 Suppl):98-112 (2000).
Calisher et al., "Antigenic relationships between flaviviruses as determined by cross-neutralization tests with polyclonal antisera," J Gen Virol. 70(Pt 1):37-43 (1989).
Di Bisceglie et al., "The unmet challenges of hepatitis C," Sci Am. 281(4):80-85 (1999).
Domingo et al., "The quasispecies (extremely heterogeneous) nature of viral RNA genome populations: biological relevance—a review," Gene. 40(1):1-8 (1985).
Dymock et al., "Novel approaches to the treatment of hepatitis C virus infection," Antivir Chem Chemother. 11(2):79-96 (2000).
Fukumoto et al., "Viral dynamics of hepatitis C early after orthotopic liver transplantation: evidence for rapid turnover of serum virions," Hepatology. 24(6):1351-1354 (1996).
Gordon et al., "Control of hepatitis C: a medicinal chemistry perspective," J Med Chem. 48(1):1-20 (2005).
International Search Report for International Application No. PCT/US2011/037305, mailed Aug. 18, 2011 (5 pages).
Martell et al., "Hepatitis C virus (HCV) circulates as a population of different but closely related genomes: quasispecies nature of HCV genome distribution," J Virol. 66(5):3225-3229 (1992).
Moennig et al., "The pestiviruses," Adv Virus Res. 41:53-98 (1992).
Moradpour et al., "Replication of hepatitis C virus," Nat Rev Microbiol. 5(6):453-463 (2007).
Nasakin et al., "Reactions of 3,3,4,4-tetracyanopyrrolidines with alcohols," Chemistry of Heterocyclic Compounds 28(11):1255-1259 (1992).

(Continued)

*Primary Examiner* — Raymond Henley, III
(74) *Attorney, Agent, or Firm* — Clark & Elbing LLP

(57) ABSTRACT

The invention is related to anti-viral compounds of formula (A) as defined in the claims, compositions containing such compounds, and therapeutic methods that include the administration of such compounds, as well to processes and intermediates useful for preparing such compounds.

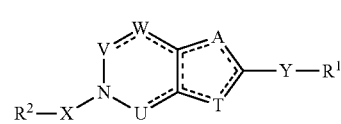

(A)

40 Claims, No Drawings

(56) References Cited

OTHER PUBLICATIONS

Neumann et al., "Hepatitis C viral dynamics in vivo and the antiviral efficacy of interferon-α therapy," Science. 282:103-107 (1998).

Scott et al., "Interferon-alpha-2b plus ribavirin: a review of its use in the management of chronic hepatitis C," Drugs. 62(3):507-556 (2002).

Varaprasad et al., "Synthesis of pyrrolo[2,3-d]pyrimidine nucleoside derivatives as potential anti-HCV agents," Bioorg Chem. 35(1):25-34 (2007).

Zhang et al., "One-pot synthesis of pyrrolo[3,2-d]pyridazines and pyrrole-2,3-diones via zirconocene-mediated four-component coupling of Si-tethered diyne, nitriles, and azide," Org Lett. 13(7):1626-1629 (2011).

Wamhoff et al., "Pyrrolo[2,3-d]-und pyrrolo[1,2-a]pyrimidine aus heterocyclischen beta-enaminoestern bzw. -nitrilen und isocyanaten und acetylaceton," Chem Ber. 109:2983-95 (1976).

Examination Report for European Patent Application No. 11724336.0, dated Jan. 27, 2014 (7 pages).

\* cited by examiner

HETEROCYCLIC FLAVIVIRIDAE VIRUS INHIBITORS

FIELD OF THE INVENTION

The present application is directed to novel inhibitors of Flaviviridae viruses, compositions containing such compounds, and therapeutic methods that include the administration of such compounds.

BACKGROUND OF THE INVENTION

Viruses of the Flaviviridae family include at least three distinguishable genera including pestiviruses, flaviviruses, and hepaciviruses (Calisher, et al., J. Gen. Virol., 1993, 70, 37-43). While pestiviruses cause many economically important animal diseases such as bovine viral diarrhea virus (BVDV), classical swine fever virus (CSFV, hog cholera) and border disease of sheep (BDV), their importance in human disease is less well characterized (Moennig, V., et al., Adv. Vir. Res. 1992, 48, 53-98). Flaviviruses are responsible for important human diseases such as dengue fever and yellow fever while hepaciviruses cause hepatitis C virus infections in humans. Other important viral infections caused by the Flaviviridae family include West Nile virus (WNV) Japanese encephalitis virus (JEV), tick-borne encephalitis virus, Junjin virus, Murray Valley encephalitis, St Louis enchaplitis, Omsk hemorrhagic fever virus and Zika virus.

Hepaciviridae include the hepatitis C virus (HCV) which is the leading cause of chronic liver disease worldwide (Boyer, N. et al. J. Hepatol. 32:98-112, 2000), so a significant focus of current antiviral research is directed toward the development of improved methods of treatment of chronic HCV infections in humans (Di Besceglie, A. M. and Bacon, B. R., Scientific American, Oct.: 80-85, (1999); Gordon, C. P., et al., J. Med. Chem. 2005, 48, 1-20; Maradpour, D.; et al., Nat. Rev. Micro. 2007, 5(6), 453-463). A number of HCV treatments are reviewed by Bymock et al. in Antiviral Chemistry & Chemotherapy, 11:2; 79-95 (2000). Virologic cures of patients with chronic HCV infection are difficult to achieve because of the prodigious amount of daily virus production in chronically infected patients and the high spontaneous mutability of HCV virus (Neumann, et al., Science 1998, 282, 103-7; Fukimoto, et al., Hepatology, 1996, 24, 1351-4; Domingo, et al., Gene, 1985, 40, 1-8; Martell, et al., J. Virol. 1992, 66, 3225-9.

Currently, there are primarily two antiviral compounds, ribavirin, a nucleoside analog, and interferon-alpha (α) (IFN), that are used for the treatment of chronic HCV infections in humans. Ribavirin alone is not effective in reducing viral RNA levels, has significant toxicity, and is known to induce anemia. The combination of IFN and ribavirin has been reported to be effective in the management of chronic hepatitis C (Scott, L. J., et al. Drugs 2002, 62, 507-556) but less than half the patients given this treatment show a persistent benefit.

Combined, infections from the Flaviviridae virus family cause significant mortality, morbidity and economic losses throughout the world. Therefore, there remains a need to develop effective treatments for Flaviviridae virus infections. The present invention relates to novel substituted heterocycles, processes for their preparation, their use to treat viral infections and their use to manufacture a medicine to treat viral infections, particularly infections with viruses belonging to the family of the Flaviviridae and more preferably infections with hepatitis-C-virus (HCV).

SUMMARY OF THE INVENTION

In one embodiment the invention provides compounds of formula (A)

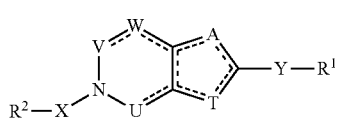

(A)

wherein:
the dotted lines represent optional double bonds, provided that no two double bonds are adjacent to one another, and that the dotted lines together represent 3 or 4 double bonds;
U is N or $CR^3$, T is N or $CR^4$, A is N or $CR^5$, W is N or $CR^6$, V is N or $CR^7$;
At least one of U, V or W is N, and
At least one of A and T is not N;
X is selected from the group consisting of $C_1$-$C_{10}$ alkylene, $C_{2-10}$ alkenylene and $C_{2-10}$ alkynylene, wherein each of said $C_1$-$C_{10}$ alkylene, $C_{2-10}$ alkenylene and $C_{2-10}$ alkynylene may have one or more carbon atoms replaced by a heteroatom selected from O, S, and N and wherein each of said $C_1$-$C_{10}$ alkylene, $C_{2-10}$ alkenylene $C_{2-10}$ alkynylene and heteroatom may be optionally substituted with 1 or more $R^{20}$;
Y is selected from the group consisting of a single bond, O, $S(O)_m$, $NR^{11}$, $C_{1-10}$ alkylene, $C_{2-10}$ alkenylene and $C_{2-10}$ alkynylene, wherein each of said $C_{1-10}$ alkylene, $C_{2-10}$ alkenylene and $C_{2-10}$ alkynylene may have one or more carbon atoms replaced by a heteroatom selected from O, S, and N;
$R^1$ is selected from the group consisting of hydrogen, aryl, heterocycle, $C_1$-$C_{10}$ alkoxy, $C_1$-$C_{10}$ thioalkyl, $C_1$-$C_{10}$ alkylamino, $C_1$-$C_{10}$ dialkylamino, $C_3$-$C_{10}$ cycloalkyl, $C_4$-$C_{10}$ cycloalkenyl and $C_4$-$C_{10}$ cycloalkynyl, wherein each of said aryl, heterocycle, $C_1$-$C_{10}$ alkoxy, $C_1$-$C_{10}$ thioalkyl, $C_1$-$C_{10}$ alkylamino, $C_1$-$C_{10}$ dialkylamino, $C_3$-$C_{10}$ cycloalkyl, $C_4$-$C_{10}$ cycloalkenyl and $C_4$-$C_{10}$ cycloalkynyl may be optionally substituted with 1 or more $R^{20}$.

$R^2$ is selected from the group consisting of aryl, aryloxy, arylthio, cycloalkyl, cycloalkenyl, cycloalkynyl, alkynyl and heterocycle, wherein each of said aryl, aryloxy, arylthio, cycloalkyl, cycloalkenyl, cycloalkynyl, alkynyl and heterocycle may be optionally substituted with one or more $R^{17}$.

$R^3$ and $R^7$ are independently selected from the group consisting of hydrogen, $C_{1-18}$ alkyl, $C_{2-18}$ alkenyl, $C_{2-18}$ alkynyl, $C_{1-18}$ alkoxy, $S(O)_m R^9$, halogen, —OH, —CN, —NO$_2$, —NR$^{13}$R$^{14}$, haloalkyloxy, haloalkyl, —C(=O)R$^9$, —C(=O)OR$^9$, —C(=S)R$^9$, SH, aryl, aryloxy, arylthio, arylalkyl, $C_{1-18}$ hydroxyalkyl, $C_{3-10}$ cycloalkyl, $C_{3-10}$ cycloalkyloxy, $C_{3-10}$ cycloalkylthio, $C_{3-10}$ cycloalkenyl, $C_{7-10}$ cycloalkynyl, (=O), (=S), =NR$^{21}$ and heterocycle, wherein each of said alkyl, cycloalkyl, alkenyl, aryl and heterocycle may be optionally substituted with 1 or more $R^{20}$.

$R^4$, $R^5$ and $R^6$ are independently selected from the group consisting of hydrogen, $C_{1-18}$ alkyl, $C_{2-18}$ alkenyl, $C_{2-18}$ alkynyl, $C_{1-18}$ alkoxy, $S(O)_m R^9$, halogen, —OH, —CN, —NO$_2$, —NR$^{13}$R$^{14}$, haloalkyloxy, haloalkyl, —C(=O)R$^9$, —C(=S)R$^9$, SH, aryl, aryloxy, arylthio, arylalkyl, $C_{1-18}$ hydroxyalkyl, $C_{3-10}$ cycloalkyl, $C_{3-10}$ cycloalkyloxy, $C_{3-10}$ cycloalkylthio, $C_{3-10}$ cycloalkenyl, $C_{7-10}$ cycloalkynyl and heterocycle, wherein each of said alkyl, cycloalkyl, alkenyl, aryl and heterocycle may be optionally substituted with 1 or more $R^{20}$.

$R^9$ and $R^{18}$ are independently selected from the group consisting of hydrogen, OH, $C_{1-18}$ alkyl, $C_{2-18}$ alkenyl, $C_{3-10}$ cycloalkyl, $C_{4-10}$ cycloalkenyl, $C_{1-18}$ alkoxy, —NR$^{15}$R$^{16}$, aryl, CH$_2$OCH(=O)R$^{9a}$, and CH$_2$OC(=O)OR$^{9a}$ where R$^{9a}$ is $C_1$-$C_{12}$ alkyl, $C_6$-$C_{20}$ aryl, $C_6$-$C_{20}$ alkylaryl or $C_6$-$C_{20}$ aralkyl;

R[11] is selected from the group consisting of hydrogen, $C_{1-18}$ alkyl, $C_{2-18}$ alkenyl, $C_{3-10}$ cycloalkyl, $C_{4-10}$ cycloalkenyl, aryl, —C(=O)R[12], and heterocycle;

R[12] is selected from the group consisting of hydrogen, $C_{1-18}$ alkyl, $C_{2-18}$ alkenyl, aryl, $C_{3-10}$ cycloalkyl, and $C_{4-10}$ cycloalkenyl;

R[13] and R[14] are independently selected from the group consisting of hydrogen, $C_{1-18}$ alkyl, $C_{2-18}$ alkenyl, aryl, $C_{2-18}$ alkynyl, $C_{3-10}$ cycloalkyl, $C_{4-10}$ cycloalkenyl, heterocycle, —C(=O)R[12]; S(O)$_m$R[9] and —C(=S)R[12], or R[13] and R[14] together with the nitrogen to which they are both attached form a heterocycle;

R[15] and R[16] are independently selected from the group consisting of hydrogen, $C_{1-18}$ alkyl, $C_{2-18}$ alkenyl, $C_{2-18}$ alkynyl, aryl, $C_{3-10}$ cycloalkyl, and $C_{4-10}$ cycloalkenyl;

R[17] is selected from the group consisting of hydrogen, $C_{1-18}$ alkyl, $C_{2-18}$ alkenyl, $C_{2-18}$ alkynyl, $C_{1-18}$ alkoxy, $C_{1-18}$ alkylthio, $C_{1-18}$ alkylsulfoxide, $C_{1-18}$ alkylsulfone, $C_{1-18}$ halogenated alkyl, $C_{2-18}$ halogenated alkenyl, $C_{2-18}$ halogenated alkynyl, $C_{1-18}$ halogenated alkoxy, $C_{1-18}$ halogenated alkylthio, $C_{3-10}$ cycloalkyl, $C_{3-10}$ cycloalkenyl, $C_{7-10}$ cycloalkynyl, halogen, OH, CN, $CO_2H$, $CO_2R^{18}$, $NO_2$, NR[13]R[14], haloalkyl, C(=O)R[18], C(=S)R[18], SH, aryl, aryloxy, arylthio, arylsulfoxide, arylsulfone, arylsulfonamide, arylalkyl, arylalkyloxy, arylalkylthio, heterocycle and $C_{1-18}$ hydroxyalkyl, where each of said aryl, aryloxy, arylthio, arylsulfoxide, arylsulfone, arylsulfonamide, arylalkyl, arylalkyloxy, arylalkylthio, heterocycle and $C_{1-18}$ hydroxyalkyl may be optionally substituted with 1 or more R[19];

R[19] is selected from the group consisting of hydrogen, $C_{1-18}$ alkyl, $C_{2-18}$ alkenyl, $C_{2-18}$ alkynyl, $C_{1-18}$ alkoxy, $C_{2-18}$ alkenyloxy, $C_{2-18}$ alkynyloxy, $C_{1-18}$ alkylthio, $C_{3-10}$ cycloalkyl, $C_{4-10}$ cycloalkenyl, $C_{4-10}$ cycloalkynyl, halogen, —OH, —CN, cyanoalkyl, —$NO_2$, —NR[13]R[14], $C_{1-18}$ haloalkyl, $C_{1-18}$ haloalkyloxy, —C(=O)R[18], —C(=O)OR[18], —OalkenylC(=O)OR[18], —OalkylC(=O)NR[15]R[16], —OalkylOC(=O)R[18], —C(=S)R[18], SH, —C(=O)N($C_{1-6}$ alkyl), —N(H)S(O)(O)($C_{1-6}$ alkyl), aryl, heterocycle, $C_{1-48}$alkylsulfone, arylsulfoxide, arylsulfonamide, aryl($C_{1-18}$)alkyloxy, aryloxy, aryl($C_{1-18}$ alkyl)oxy, arylthio, aryl($C_{1-18}$)alkylthio and aryl($C_{1-18}$)alkyl, wherein aryl, heterocycle, $C_{1-18}$alkylsulfone, arylsulfoxide, arylsulfonamide, aryl($C_{1-18}$)alkyloxy, aryloxy, aryl($C_{1-18}$ alkyl)oxy, arylthio, aryl($C_{1-18}$)alkylthio and aryl($C_{1-18}$)alkyl may be optionally substituted with 1 or more R[20].

R[20] is selected from the group consisting of hydrogen, $C_{1-18}$ alkyl, $C_{2-18}$ alkenyl, $C_{2-18}$ alkynyl, heterocycle, $C_{1-18}$ alkoxy, $C_{1-18}$ alkylthio, $C_{1-18}$ alkylsulfoxide, $C_{1-18}$ alkylsulfone, $C_{1-18}$ halo-alkyl, $C_{2-18}$ halo-alkenyl, $C_{2-18}$ halo-alkynyl, $C_{1-18}$ halo-alkoxy, $C_{1-18}$ halo-alkylthio, $C_{3-10}$ cycloalkyl, $C_{3-10}$ cycloalkenyl, $C_{7-10}$ cycloalkynyl, halogen, OH, CN, oxo, cyanoalkyl, —$CO_2R^{18}$, $NO_2$, —NR[13]R[14], $C_{1-18}$ haloalkyl, C(=O)R[18], C(=S)R[18], SH, aryl, aryloxy, arylthio, arylsulfoxide, arylsulfone, arylsulfonamide, aryl($C_{1-18}$)alkyl, aryl($C_{1-18}$)alkyloxy, aryl($C_{1-18}$)alkylthio and $C_{1-18}$ hydroxyalkyl;

R[21] is selected from the group consisting of hydrogen, $C_{1-18}$ alkyl, $C_{3-10}$ cycloalkyl, $C_{1-18}$ alkoxy, ($C_{3-10}$ cycloalkyl)-$C_{1-6}$ alkyl, aryl and aryl $C_{1-18}$ alkyl;

m is an integer from 0 to 2;

and the salts, tautomers, isomers, prodrugs and solvates thereof.

In one embodiment the invention provides a compound of formula A wherein either, but not both A or T is N and wherein all other substituents are as defined as for compounds of formula A.

In one embodiment the invention provides a compound which is a compound of formula A1 wherein all other substituents are as defined as for compounds of formula A.

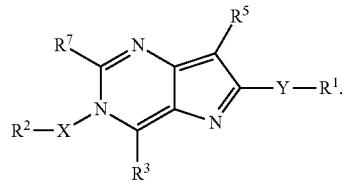

A1

In one embodiment the invention provides a compound which is a compound of formula A2 wherein all other substituents are as defined as for compounds of formula A.

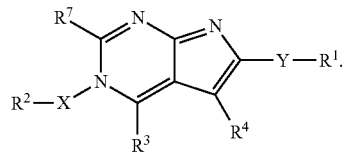

A2

In one embodiment the invention provides a compound which is a compound of formula A3 wherein all other substituents are as defined as for compounds of formula A.

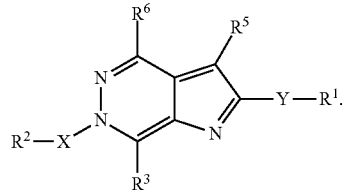

A3

In one embodiment the invention provides a compound which is a compound of formula A4 wherein all other substituents are as defined as for compounds of formula A.

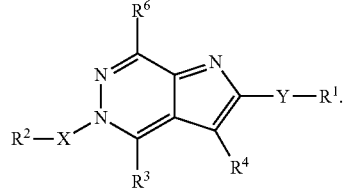

A4

In one embodiment the invention provides a compound which is a compound of formula A5 wherein all other substituents are as defined as for compounds of formula A.

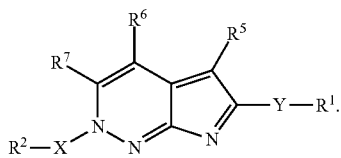

In one embodiment the invention provides a compound which is a compound of formula A6 wherein all other substituents are as defined as for compounds of formula A.

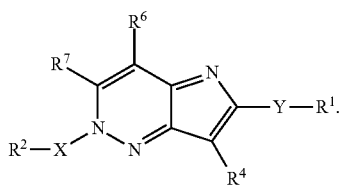

In one embodiment the invention provides a compound which is a compound of formula A7 wherein all other substituents are as defined as for compounds of formula A.

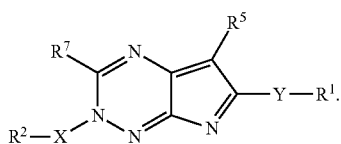

In one embodiment the invention provides a compound which is a compound of formula A8 wherein all other substituents are as defined as for compounds of formula A.

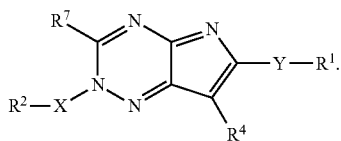

In one embodiment of the invention Y is a bond.

In one embodiment of the invention $R^1$ is aryl or heterocycle, wherein each of said aryl or heterocycle may be optionally substituted with 1 or more $R^{20}$.

In one embodiment of the invention $R^{20}$ is selected from the group consisting of hydrogen, $C_{1-18}$ alkyl, $C_{2-18}$ alkenyl, $C_{2-18}$ alkynyl, $C_{1-18}$ alkoxy, $C_{1-18}$ alkylthio, $C_{1-18}$ alkylsulfoxide, $C_{1-18}$ alkylsulfone, $C_{1-18}$ halo-alkyl, $C_{2-18}$ halo-alkenyl, $C_{2-18}$ halo-alkynyl, $C_{1-18}$ halo-alkoxy, $C_{1-18}$ halo-alkylthio, $C_{3-10}$ cycloalkyl, $C_{3-10}$ cycloalkenyl, $C_{7-10}$ cycloalkynyl, halogen, CN, oxo, cyanoalkyl, $C_{1-18}$ haloalkyl, $C(=O)R^{18}$, $C(=S)R^{18}$, and $C_{1-18}$ hydroxyalkyl.

In one embodiment of the invention $R^1$ is phenyl wherein the phenyl is independently substituted with a member of the group the group consisting of halogen and $C_1$ to $C_5$ alkyl.

In one embodiment of the invention X is methylene wherein the methylene may be optionally substituted with 1 or more $R^{20}$.

In one embodiment of the invention $R^{20}$ is selected from the group consisting of hydrogen, $C_{1-18}$ alkyl, $C_{2-18}$ alkenyl, $C_{2-18}$ alkynyl, halogen, OH, CN, cyanoalkyl and $C_{1-18}$ haloalkyl;

In one embodiment of the invention $R^2$ is selected from the group consisting of aryl and heterocycle wherein aryl and heterocycle may be optionally substituted with 1 or more $R^{17}$.

In one embodiment of the invention $R^2$ is selected from the group consisting of

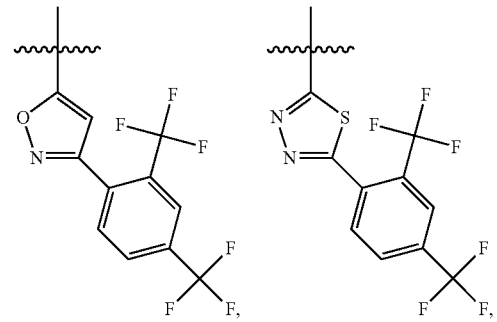

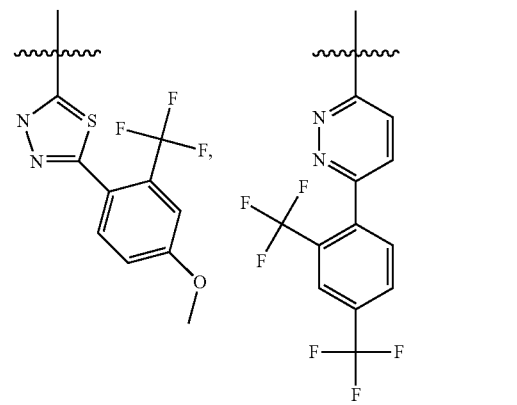

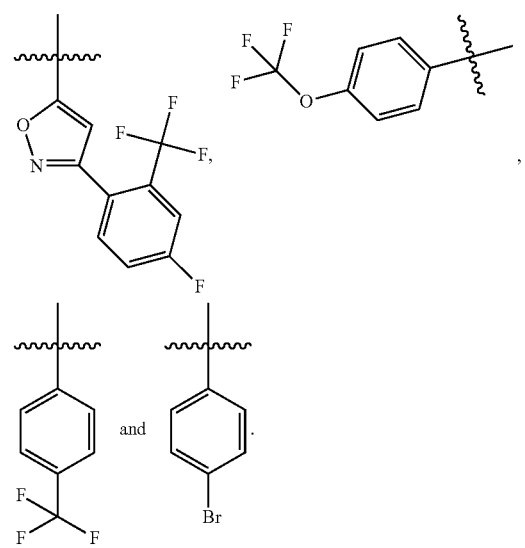

In one embodiment the invention provides a compound selected from the group consisting of

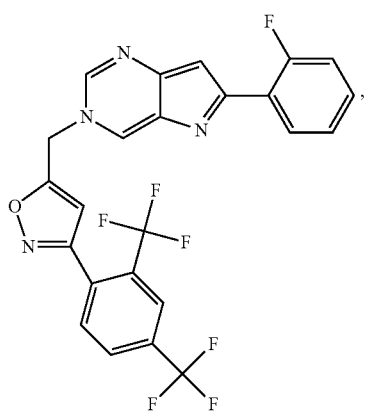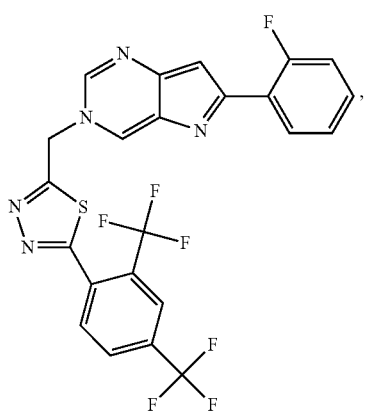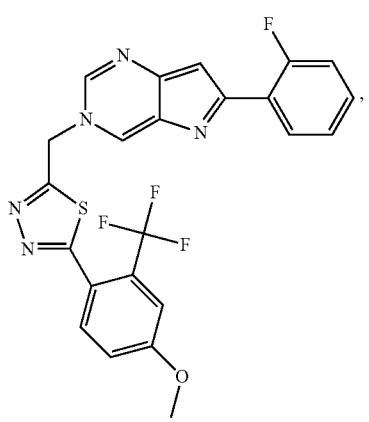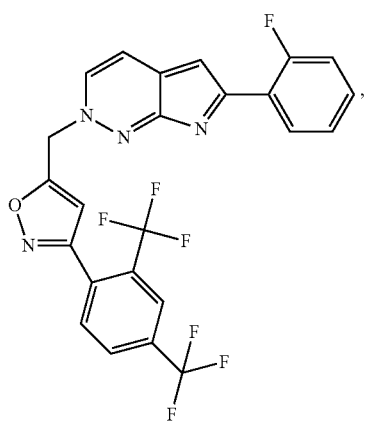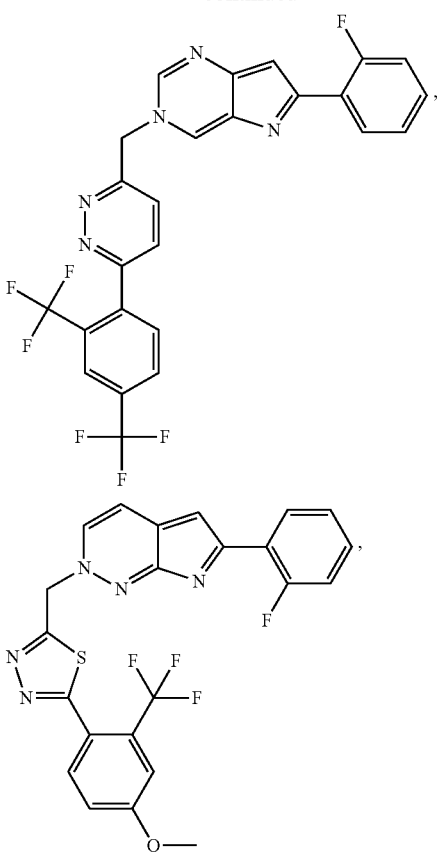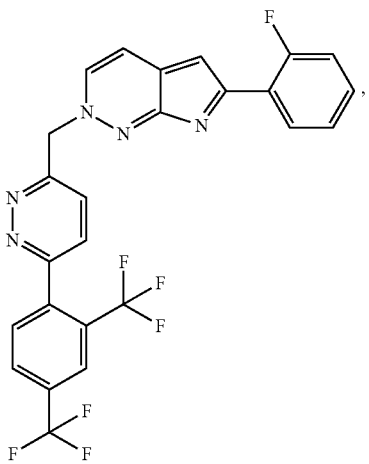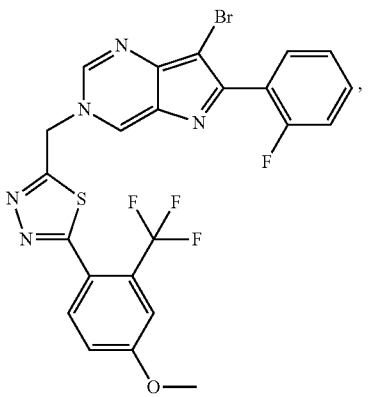

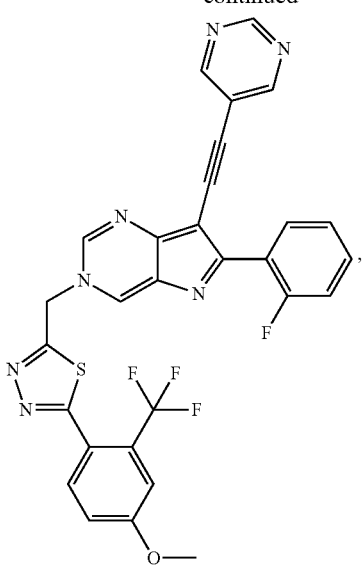

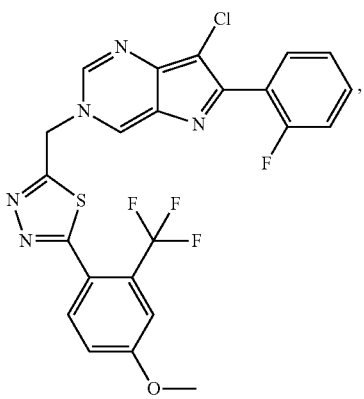

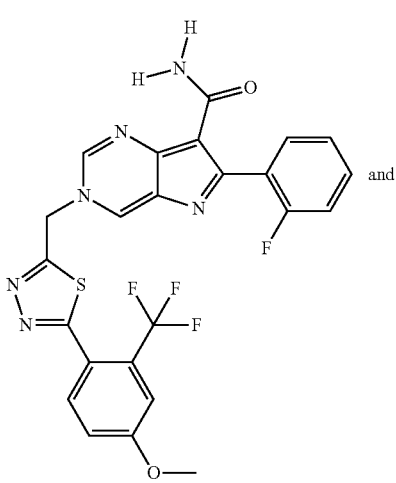

and

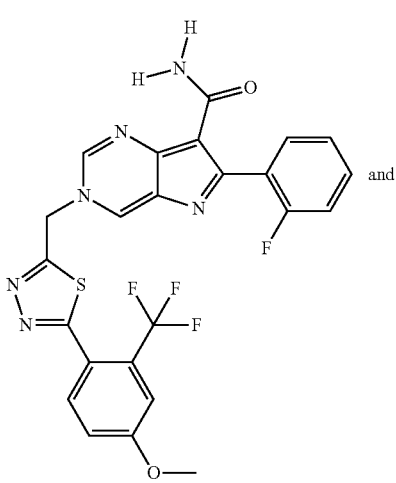

In one embodiment the invention provides a prodrug, or a pharmaceutically acceptable salt of a compound described herein.

In one embodiment the invention provides a pharmaceutical composition comprising a compound described herein or a pharmaceutically acceptable salt, or prodrug thereof; and at least one pharmaceutically acceptable carrier.

In one embodiment the invention provides a pharmaceutical composition for use in treating HCV infection comprising a compound described herein or a pharmaceutically acceptable salt, or prodrug thereof and at least one pharmaceutically acceptable carrier.

In one embodiment the invention provides a pharmaceutical composition comprising a compound described herein or a pharmaceutically acceptable salt, or prodrug thereof, at least one pharmaceutically acceptable carrier, and further comprising at least one additional therapeutic agent.

In one embodiment the invention provides a pharmaceutical composition comprising a compound described herein or a pharmaceutically acceptable salt, or prodrug thereof, at least one pharmaceutically acceptable carrier, and further comprising at least one additional therapeutic agent wherein said additional therapeutic agent is selected from the group consisting of interferons, ribavirin analogs, NS5a inhibitors, NS4b inhibitors, NS3 protease inhibitors, NS5b polymerase inhibitors, alpha-glucosidase 1 inhibitors, hepatoprotectants, non-nucleoside inhibitors of HCV, and other drugs for treating HCV.

In one embodiment the invention provides a pharmaceutical composition comprising a compound described herein or a pharmaceutically acceptable salt, or prodrug thereof, at least one pharmaceutically acceptable carrier, and further comprising at least one additional therapeutic agent selected from the group consisting of pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-nl (Wellferon), interferon alpha-n3 (Alferon), interferon-beta (Avonex, DL-8234), interferon-omega (omega DUROS, Biomed 510), albinterferon alpha-2b (Albuferon), IFN alpha XL, BLX-883 (Locteron), DA-3021, glycosylated interferon alpha-2b (AVI-005), PEG-Infergen, PEGylated interferon lambda (PEGylated IL-29), and belerofon.

In one embodiment the invention provides a pharmaceutical composition comprising a compound described herein or a pharmaceutically acceptable salt, or prodrug thereof, at least one pharmaceutically acceptable carrier, and further comprising at least one additional therapeutic agent selected from the group consisting of ribavirin (Rebetol, Copegus), and taribavirin (Viramidine).

In one embodiment the invention provides a pharmaceutical composition comprising a compound described herein or a pharmaceutically acceptable salt, or prodrug thereof, at least one pharmaceutically acceptable carrier, and further comprising at least one additional therapeutic agent selected from the group consisting of boceprevir (SCH-503034, SCH-7), telaprevir (VX-950), VX-813, TMC-435 (TMC435350), ABT-450, BI-201335, BI-1230, MK-7009, SCH-900518, VBY-376, VX-500, GS-9256, GS-9451, BMS-790052, BMS-605339, PHX-1766, AS-101, YH-5258, YH5530, YH5531, and ITMN-191 (R-7227).

In one embodiment the invention provides a pharmaceutical composition comprising a compound described herein or a pharmaceutically acceptable salt, or prodrug thereof, at least one pharmaceutically acceptable carrier, and further comprising at least one additional therapeutic agent selected from the group consisting of celgosivir (MX-3253), Miglitol, and UT-231B.

In one embodiment the invention provides a pharmaceutical composition comprising a compound described herein or a pharmaceutically acceptable salt, or prodrug thereof, at least one pharmaceutically acceptable carrier, and further comprising at least one additional therapeutic agent selected from the group consisting of emericasan (IDN-6556), ME-3738, GS-9450 (LB-84451), silibilin, and MitoQ, nucleoside or nucleotide inhibitors of HCV NS5B polymerase, R1626, R7128 (R4048), IDX184, IDX-102, PSI-7851, BCX-4678, valopicitabine (NM-283), PSI-7977, and MK-0608.

In one embodiment the invention provides a pharmaceutical composition comprising a compound described herein or a pharmaceutically acceptable salt, or prodrug thereof, at least one pharmaceutically acceptable carrier, and further comprising at least one additional therapeutic agent selected from the group consisting of filibuvir (PF-868554), ABT-333, ABT-072, BI-207127, VCH-759, VCH-916, JTK-652, MK-3281, GS-9190 (tegobuvir), VBY-708, VCH-222, A848837, ANA-598, GL60667, GL59728, A-63890, A-48773, A-48547, BC-2329, VCH-796 (nesbuvir), GSK625433, BILN-1941, XTL-2125, and tegobuvir.

In one embodiment the invention provides a pharmaceutical composition comprising a compound described herein or a pharmaceutically acceptable salt, or prodrug thereof, at least one pharmaceutically acceptable carrier, and further comprising at least one additional therapeutic agent selected from the group consisting of AZD-2836 (A-831), AZD-7295 (A-689), GS-5885, and BMS-790052.

In one embodiment the invention provides a pharmaceutical composition comprising a compound described herein or a pharmaceutically acceptable salt, or prodrug thereof, at least one pharmaceutically acceptable carrier, and further comprising at least one additional therapeutic agent selected from the group consisting of imiquimod, 852A, GS-9524, ANA-773, ANA-975, AZD-8848 (DSP-3025), PF-04878691, and SM-360320, cyclophillin inhibitors, (DE-BIO-025, SCY-635), and NIM811 and HCV IRES inhibitors (MCI-067).

In one embodiment the invention provides a pharmaceutical composition comprising a compound described herein or a pharmaceutically acceptable salt, or prodrug thereof, at least one pharmaceutically acceptable carrier, and further comprising at least one additional therapeutic agent selected from the group consisting of BAS-100, SPI-452, PF-4194477, TMC-41629, GS-9350, GS-9585, and roxythromycin.

In one embodiment the invention provides a pharmaceutical composition comprising a compound described herein or a pharmaceutically acceptable salt, or prodrug thereof, at least one pharmaceutically acceptable carrier, and further comprising at least one additional therapeutic agent from the group consisting of thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, FK-788, CTS-1027, SD-101, BMS-824393, MK-5172, and VX-497 (merimepodib).

In one embodiment the invention provides a pharmaceutical composition comprising a compound described herein or a pharmaceutically acceptable salt, or prodrug thereof, at least one pharmaceutically acceptable carrier, and further comprising at least one additional therapeutic agent comprising a nucleoside analogue.

In one embodiment the invention provides a pharmaceutical composition comprising a compound described herein or a pharmaceutically acceptable salt, or prodrug thereof, at least one pharmaceutically acceptable carrier, and further comprising at least one additional therapeutic agent comprising an interferon or pegylated interferon.

In one embodiment the invention provides a pharmaceutical composition comprising a compound described herein or a pharmaceutically acceptable salt, or prodrug thereof, at least one pharmaceutically acceptable carrier, and further comprising at least one additional therapeutic agent comprising a nucleoside analogue wherein said nucleoside analogue is selected from ribavirin, viramidine, levovirin, a L-nucleoside, and isatoribine and said interferon is α-interferon or pegylated interferon.

In one embodiment the invention provides a method of treating HCV infection, said method comprising administering to an individual a pharmaceutical composition which comprises a therapeutically effective amount of a compound described herein or a pharmaceutically acceptable salt, or prodrug thereof.

In one embodiment the invention provides a compound or synthetic method described herein.

In one embodiment the invention provides a compound as described herein or a pharmaceutically acceptable salt, or prodrug thereof for use in medical therapy.

In one embodiment the invention provides for the use of a compound as described herein or a pharmaceutically acceptable salt, or prodrug thereof for preparing a medicament for treating HCV infection in an animal.

In one embodiment the invention provides for the use of a compound as described herein or a pharmaceutically acceptable salt, or prodrug thereof for use in the prophylactic or therapeutic treatment of HCV infection.

COMPOUNDS OF THE INVENTION

The compounds of the invention exclude compounds heretofore known. However it is within the invention to use compounds that previously were not known to have antiviral properties for antiviral purposes (e.g. to produce an anti-viral effect in an animal). With respect to the United States, the compounds or compositions herein exclude compounds that are anticipated under 35 USC §102 or that are obvious under 35 USC §103.

Whenever a compound described herein is substituted with more than one of the same designated group, e.g., "$R^1$", then it will be understood that the groups may be the same or different, i.e., each group is independently selected.

"Alkyl" means a hydrocarbon containing normal, secondary, tertiary or cyclic carbon atoms. Examples include, but are not limited to methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), and 3,3-dimethyl-2-butyl (—CH(CH$_3$)C(CH$_3$)$_3$).

"Alkenyl" means a hydrocarbon containing normal, secondary, tertiary or cyclic carbon atoms with at least one site of unsaturation, i.e. a carbon-carbon, sp$^2$ double bond. Examples include, but are not limited to, ethylene or vinyl (—CH=CH$_2$), allyl (—CH$_2$CH=CH$_2$), cyclopentenyl (—C$_5$H$_7$), and 5-hexenyl (—CH$_2$CH$_2$CH$_2$CH$_2$CH=CH$_2$).

"Alkynyl" means a hydrocarbon containing normal, secondary, tertiary or cyclic carbon atoms with at least one site of unsaturation, i.e. a carbon-carbon, sp triple bond. Examples include, but are not limited to, acetylenic (—C≡CH) and propargyl (—CH$_2$C≡CH), "Alkylene" means a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to, methylene (—CH$_2$—) 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like.

"Alkenylene" means an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to, 1,2-ethylene (—CH=CH—).

"Alkynylene" means an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to, acetylene (—C≡C—), propargyl (—CH$_2$C≡C—), and 4-pentynyl (—CH$_2$CH$_2$CH$_2$C≡CH—).

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, naphthalene, anthracene, biphenyl, and the like.

"Arylalkyl" means an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group comprises 6 to 20 carbon atoms, e.g., the alkyl moiety, including alkanyl, alkenyl or alkynyl groups, of the arylalkyl group is 1 to 6 carbon atoms and the aryl moiety is 5 to 14 carbon atoms.

"Heterocyclylalkyl" means an acyclic alkyl radical in which one of the hydrogen atoms bonded to a carbon atom, typically a terminal or sp$^3$ carbon atom, is replaced with an heterocycle radical.

The term "polycarbocycle" means a saturated or unsaturated polycyclic ring system having from about 6 to about 25 carbon atoms and having two or more rings (e.g. 2, 3, 4, or 5 rings). The rings can be fused and/or bridged to form the polycyclic ring system. For example, the term includes bicyclo [4,5], [5,5], [5,6] or [6,6] ring systems, as well as the following bridged ring systems:

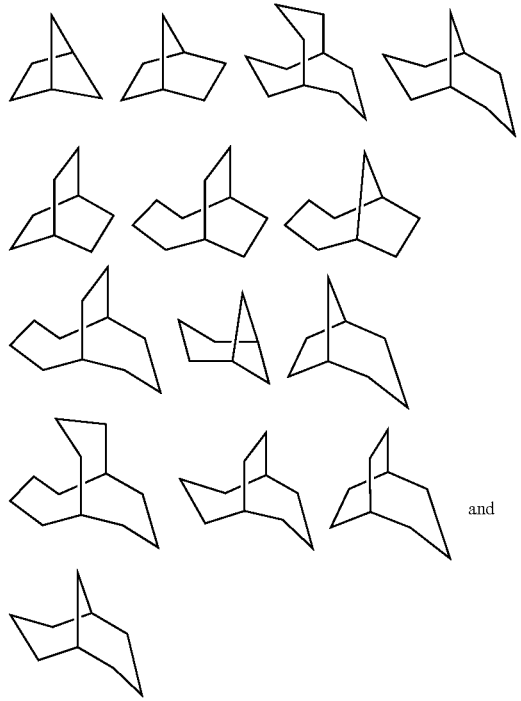

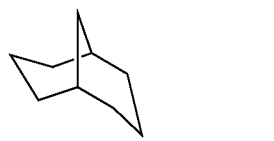

and (i.e., [2.1.1], [2.2.1], [3.3.3], [4.3.1], [2.2.2], [4.2.2], [4.2.1], [4.3.2], [3.1.1], [3.2.1], [4.3.3], [3.3.2], [3.2.2] and [3.3.1] polycyclic rings, respectively) that can be linked to the remainder of the compound of formula (I) through any synthetically feasible position. Like the other polycarbocycles, these representative bicyclo and fused ring systems can optionally comprise one or more double bonds in the ring system.

The term "polyheterocycle" means a polycarbocycle as defined herein, wherein one or more carbon atoms is replaced with a heteroatom (e,g, O, S, S(O), S(O)$_2$, N$^+$(O$^-$)R$_x$, or NR$_x$); wherein each of said R$_1$ is independently H, (C1-10)alkyl, (C2-10)alkenyl, (C2-10)alkynyl, (C1-10)alkanoyl, S(O)$_2$ NR$_n$R$_p$, S(O)$_2$R$_x$, or (C1-10)alkoxy, wherein each of said (C1-10)alkyl, (C2-10)alkenyl, (C2-10)alkynyl, (C1-10)alkanoyl, and (C1-10)alkoxy is optionally substituted with one or more halo).

The term "optionally substituted" in reference to a particular moiety of a compound (e.g., an optionally substituted aryl group) refers to a moiety having 0, 1, 2, or more substituents.

The symbol " ----- " means that a bond is a single or double bond. In a non-limiting example,

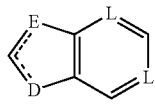

can be

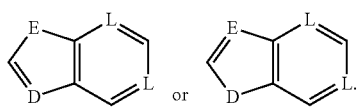

"Haloalkyl" means an alkyl group substituted with one or more halogens (e.g. F, Cl, Br, or I). Representative examples of haloalkyl include trifluoromethyl, 2,2,2-trifluoroethyl, and 2,2,2-trifluoro-1-(trifluoromethyl)ethyl.

"Heterocycle" as used herein includes by way of example and not limitation these heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (O, N, P or S).

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4H-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

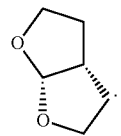

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" refers to a saturated, unsaturated or aromatic ring having up to about 25 carbon atoms which is uninterrupted by any heteroatoms. Typically, a carbocycle has about 3 to 7 carbon atoms as a monocycle, about 7 to 12 carbon atoms as a bicycle, and up to about 25 carbon atoms as a polycycle. Monocyclic carbocycles typically have 3 to 6 ring atoms, still more typically 5 or 6 ring atoms. Bicyclic carbocycles typically have 7 to 12 ring atoms, e.g., arranged as a bicyclo [4,5], [5,5], [5,6] or [6,6] system, or 9 or 10 ring atoms arranged as a bicyclo [5,6] or [6,6] system. The term carbocycle includes "cycloalkyl" which is a saturated or unsaturated carbocycle. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl.

The prefix "$C_p$-$C_q$", where p and q are integers designates the range of carbon atoms comprised by the subsequently named substituent. For example, in the term "$C_1$-$C_{10}$ alkyl", p is 1 and q is 10, and this term refers to an alkyl group comprising 1, 2, 3, 4, 5, 6, 7, 8, 9 or 10 carbon atoms.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The term "treatment" or "treating," to the extent it relates to a disease or condition includes preventing the disease or condition from occurring, inhibiting the disease or condition, eliminating the disease or condition, and/or relieving one or more symptoms of the disease or condition.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. The invention includes all stereoisomers of the compounds described herein.

Prodrugs

The term "prodrug" as used herein refers to any compound that when administered to a biological system generates the drug substance, i.e. active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically-active compound.

"Prodrug moiety" refers to a labile functional group which separates from the active inhibitory compound during metabolism, systemically, or inside a cell, by hydrolysis, enzymatic cleavage, or by some other process inside the organism (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191). Enzymes which are capable of an enzymatic activation mechanism include, but are not limited to, amidases, esterases, microbial enzymes, phospholipases, cholinesterases, and phosphates. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters —$CH_2C(=O)R^x$ and acyloxymethyl carbonates —$CH_2C(=O)OR^x$ where $R^x$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al. (1983) *J. Pharm. Sci.* 72: 324; also U.S. Pat. Nos. 4,816,570, 4,968, 788, 5,663,159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —$CH_2C(=O)C(CH_3)_3$. An exemplary acyloxymethyl carbonate prodrug moiety is pivaloyloxymethylcarbonate (POC) —$CH_2C(=O)OC(CH_3)_3$.

Aryl esters of phosphorus groups, especially phenyl esters, are reported to enhance oral bioavailability (De Lombaert et al. (1994) *J. Med. Chem.* 37: 498). Phenyl esters containing a carboxylic ester ortho to a phosphate have also been described (Khamnei and Torrence, (1996) *J. Med. Chem.* 39:4109-4115). Benzyl esters are reported to generate parent phosphonic acids. In some cases, substituents at the ortho- or para-position may accelerate the hydrolysis. Benzyl analogs with an acylated phenol or an alkylated phenol may generate the phenolic compound through the action of enzymes, e.g., esterases, oxidases, etc., which in turn undergoes cleavage at the benzylic C—O bond to generate phosphoric acid and a quinone methide intermediate. Examples of this class of prodrugs are described by Mitchell et al. (1992) *J. Chem. Soc. Perkin Trans. II* 2345; Glazier WO 91/19721. Still other benzylic prodrugs have been described containing a carboxylic ester-containing group attached to the benzylic methylene (Glazier WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al. (1993) *Antiviral Res.*, 22: 155-174; Benzaria et al. (1996) *J. Med. Chem.* 39: 4958).

Protecting Groups

In the context of the present invention, protecting groups include prodrug moieties and chemical protecting groups.

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group will be dependent upon the chemistry of the reaction to be protected against (e.g., acidic, basic, oxidative, reductive or other conditions) and the intended direction of the synthesis. The protecting groups do not need to be, and generally are not, the same if the compound is substituted with multiple protecting groups. In general, protecting groups will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene (John Wiley & Sons, Inc., New York, 1991, ISBN 0-471-62301-6) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below.

Whenever a compound described herein is substituted with more than one of the same designated group, e.g., "$R^1$", then it will be understood that the groups may be the same or different, i.e., each group is independently selected. Wavy lines indicate the site of covalent bond attachments to the adjoining groups, moieties, or atoms.

In one embodiment of the invention, the compound is in an isolated and purified form. Generally, the term "isolated and purified" means that the compound is substantially free from biological materials (e.g. blood, tissue, cells, etc.). In one specific embodiment of the invention, the term means that the compound or conjugate of the invention is at least about 50 wt. % free from biological materials; in another specific embodiment, the term means that the compound or conjugate of the invention is at least about 75 wt. % free from biological materials; in another specific embodiment, the term means that the compound or conjugate of the invention is at least about 90 wt. % free from biological materials; in another specific embodiment, the term means that the compound or conjugate of the invention is at least about 98 wt. % free from biological materials; and in another embodiment, the term means that the compound or conjugate of the invention is at least about 99 wt. % free from biological materials. In another specific embodiment, the invention provides a compound or conjugate of the invention that has been synthetically prepared (e.g., ex vivo).

Stereoisomers

The compounds of the invention may have chiral centers, e.g., chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Salts and Hydrates

Examples of physiologically acceptable salts of the compounds of the invention include salts derived from an appropriate base, such as an alkali metal (for example, sodium), an alkaline earth metal (for example, magnesium), ammonium and $NX_4^+$ (wherein X is $C_1$-$C_4$ alkyl). Physiologically acceptable salts of a hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound of a hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds of the invention will typically be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

Metal salts typically are prepared by reacting the metal hydroxide with a compound of this invention. Examples of metal salts which are prepared in this way are salts containing Li⁺, Na⁺, and K⁺. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the natural or unnatural amino acids are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Methods of Inhibition of HCV

Another aspect of the invention relates to methods of inhibiting the activity of HCV comprising the step of treating a sample suspected of containing HCV with a compound or composition of the invention.

Compounds of the invention may act as inhibitors of HCV, as intermediates for such inhibitors or have other utilities as described below. Accordingly, the invention relates to methods of detecting HCV in a sample suspected of containing HCV comprising the steps of: treating a sample suspected of containing HCV with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl or amino. In one embodiment the invention provides a compound of formula (A) that comprises or that is bound or linked to one or more detectable labels. Within the context of the invention samples suspected of containing HCV include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing HCV. Samples can be contained in any medium including water and organic solvent/water mixtures. Samples include living organisms such as humans, and man made materials such as cell cultures.

The treating step of the invention comprises adding the compound of the invention to the sample or it comprises adding a precursor of the composition to the sample. The addition step comprises any method of administration as described above.

If desired, the activity of HCV after application of the compound can be observed by any method including direct and indirect methods of detecting HCV activity. Quantitative, qualitative, and semiquantitative methods of determining HCV activity are all contemplated. Typically one of the screening methods described above are applied, however, any other method such as observation of the physiological properties of a living organism are also applicable.

Many organisms contain HCV. The compounds of this invention are useful in the treatment or prophylaxis of HCV activation in animals or in man.

However, in screening compounds capable of inhibiting HCV it should be kept in mind that the results of enzyme assays may not always correlate with cell culture assays. Thus, a cell based assay should typically be the primary screening tool.

Pharmaceutical Formulations

The compounds of this invention are typically formulated with conventional carriers and excipients, which will be selected in accord with ordinary practice. Tablets typically will contain excipients, glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s)

in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of HCV infection.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provides compositions comprising one or more compounds of the invention formulated for sustained or controlled release.

Methods of Treatment

As used herein, the term "therapeutically effective amount" refers to an amount of a compound of the invention that is effective to ameliorate at least one symptom of HCV infection in a human being. Thus, for example, in some HCV infected individuals a therapeutically effective amount of a compound of the invention is effective to reduce by a statistically significant amount the viral load of HCV viral particles present in the body of the infected person. Viral load can be measured, for example, by measuring plasma HCV RNA levels using, for example, the COBAS TaqMan HCV assay (Roche Molecular Systems). Typically, an HCV infected person who is treated with a compound of the invention in accordance with the present invention experiences an improvement in one or all of the symptoms associated with the HCV infection. For example, an HCV patient may experience an improvement in one or all of the following symptoms that can be associated with HCV infection: fever, headache, muscle aches, fatigue, loss of appetite, nausea, vomiting and diarrhea.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies. It can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Another aspect of the present invention includes use of a compound of the present invention for the manufacture of a medicament for the treatment of an HCV viral infection. Another aspect includes a compound for use in treating a viral infection. In one embodiment of each aspect of use and compound, the treatment results in one or more of a reduction in viral load or clearance of viral RNA.

Another aspect of the present invention includes a method for treating or preventing HCV comprising administering a compound of the present invention. Another aspect includes the use of a compound of the present invention for the manufacture of a medicament for the treatment or prevention of HCV.

Combination Therapy

Active ingredients of the invention can also be used in combination with other active ingredients. Such combinations are selected based on the condition to be treated, cross-reactivities of ingredients and pharmaco-properties of the combination. Typically, the active ingredients of this invention will be combined with other agents having anti-HCV activity, but may also be combined with agents having immunomodulatory activity as well.

It is also possible to combine any compound of the invention with one or more other active ingredients in a unitary dosage form for simultaneous or sequential administration to a patient. The combination therapy may be administered as a simultaneous or sequential regimen. When administered sequentially, the combination may be administered in two or more administrations.

The combination therapy may provide "synergy" and "synergistic effect", i.e. the effect achieved when the active ingredients which are used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

Suitable active therapeutic agents or ingredients which can be combined with the compounds of formula A can include:

1) interferons, e.g., pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha XL, BLX-883 (Locteron), DA-3021, glycosylated interferon alpha-2b (AVI-005), PEG-Infergen, PEGylated interferon lambda (PEGylated IL-29), and belerofon, 2) ribavirin and its analogs, e.g., ribavirin (Rebetol, Copegus), and taribavirin (Viramidine), 3) HCV NS3 protease inhibitors, e.g., boceprevir (SCH-503034, SCH-7), telaprevir (VX-950), VX-813, TMC-435 (TMC435350), ABT-450, BI-201335, BI-1230, MK-7009, SCH-900518, VBY-376, VX-500, GS-9256, GS-9451, BMS-790052, BMS-605339, PHX-1766, AS-101, YH-5258, YH5530, YH5531, and ITMN-191 (R-7227), 4) alpha-glucosidase 1 inhibitors, e.g., celgosivir (MX-3253), Miglitol, and UT-231B, 5) hepatoprotectants, e.g., emericasan (IDN-6556), ME-3738, GS-9450 (LB-84451), silibilin, and MitoQ, 6) nucleoside or nucleotide inhibitors of HCV NS5B polymerase, e.g., R1626, R7128 (R4048), IDX184, IDX-102, PSI-7851, BCX-4678, valopicitabine (NM-283), PSI-7977, and MK-0608, 7) non-nucleoside inhibitors of HCV NS5B polymerase, e.g., filibuvir (PF-868554), ABT-333, ABT-072, BI-207127, VCH-759, VCH-916, JTK-652, MK-3281, tegobuvir, VBY-708, VCH-222, A848837, ANA-598, GL60667, GL59728, A-63890, A-48773, A-48547, BC-2329, VCH-796 (nesbuvir), GSK625433, BILN-1941, XTL-2125, and tegobuvir, 8) HCV NS5A inhibitors, e.g., AZD-2836 (A-831), AZD-7295 (A-689), GS-5885, and BMS-790052, 9) TLR-7 agonists, e.g., imiquimod, 852A, GS-9524, ANA-773, ANA-975, AZD-8848 (DSP-3025), PF-04878691, and SM-360320, 10) cyclophillin inhibitors, e.g., DEBIO-025, SCY-635, and NIM811, 11) HCV IRES inhibitors, e.g., MCI-067, 12) pharmacokinetic enhancers, e.g., BAS-100, SPI-452, PF-4194477, TMC-41629, GS-9350, GS-9585, and roxythromycin, 13) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, FK-788, CTS-1027, SD-101, BMS-824393, MK-5172, and VX-497 (merimepodib).

In yet another embodiment, the present application discloses pharmaceutical compositions comprising a compound of the present invention, or a pharmaceutically acceptable salt, solvate, and/or ester thereof, in combination with at least one additional therapeutic agent, and a pharmaceutically acceptable carrier or excipient.

According to the present invention, the therapeutic agent used in combination with the compound of the present invention can be any agent having a therapeutic effect when used in combination with the compound of the present invention. For example, the therapeutic agent used in combination with the compound of the present invention can be interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV.

In another embodiment, non-limiting examples of suitable combinations include combinations of one or more compounds of the present invention with one or more interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs for treating HCV.

More specifically, one or more compounds of the present invention may be combined with one or more compounds selected from the group consisting of 1) interferons, e.g., pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha XL, BLX-883 (Locteron), DA-3021, glycosylated interferon alpha-2b (AVI-005), PEG-Infergen, PEGylated interferon lambda (PEGylated IL-29), and belerofon, 2) ribavirin and its analogs, e.g., ribavirin (Rebetol, Copegus), and taribavirin (Viramidine), 3) HCV NS3 protease inhibitors, e.g., boceprevir (SCH-503034, SCH-7), telaprevir (VX-950), VX-813, TMC-435 (TMC435350), ABT-450, BI-201335, BI-1230, MK-7009, SCH-900518, VBY-376, VX-500, GS-9256, GS-9451, BMS-790052, BMS-605339, PHX-1766, AS-101, YH-5258, YH5530, YH5531, and ITMN-191 (R-7227), 4) alpha-glucosidase 1 inhibitors, e.g., celgosivir (MX-3253), Miglitol, and UT-231B, 5) hepatoprotectants, e.g., emericasan (IDN-6556), ME-3738, GS-9450 (LB-84451), silibilin, and MitoQ, 6) nucleoside or nucleotide inhibitors of HCV NS5B polymerase, e.g., R1626, R7128 (R4048), IDX184, IDX-102, PSI-7851, BCX-4678, valopicitabine (NM-283), PSI-7977, and MK-0608, 7) non-nucleoside inhibitors of HCV NS5B polymerase, e.g., filibuvir (PF-868554), ABT-333, ABT-072, BI-207127, VCH-759, VCH-916, JTK-652, MK-3281, tegobuvir, VBY-708, VCH-222, A848837, ANA-598, GL60667, GL59728, A-63890, A-48773, A-48547, BC-2329, VCH-796 (nesbuvir), GSK625433, BILN-1941, XTL-2125, and tegobuvir, 8) HCV NS5A inhibitors, e.g., AZD-2836 (A-831), AZD-7295 (A-689), GS-5885, and BMS-790052, 9) TLR-7 agonists, e.g., imiquimod, 852A, GS-9524, ANA-773, ANA-975, AZD-8848 (DSP-3025), PF-04878691, and SM-360320, 10) cyclophillin inhibitors, e.g., DEBIO-025, SCY-635, and NIM811, 11) HCV IRES inhibitors, e.g., MCI-067, 12) pharmacokinetic enhancers, e.g., BAS-100, SPI-452, PF-4194477, TMC-41629, GS-9350, GS-9585, and roxythromycin, 13) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, FK-788, CTS-1027, SD-101, BMS-824393, MK-5172, and VX-497 (merimepodib).

In yet another embodiment, the present application provides a combination pharmaceutical agent comprising:

a) a first pharmaceutical composition comprising a compound of the present invention, or a pharmaceutically acceptable salt, solvate, or ester thereof; and b) a second pharmaceutical composition comprising at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, alpha-glucosidase 1 inhibitors, hepatoprotectants, non-nucleoside inhibitors of HCV, and other drugs for treating HCV, and combinations thereof.

Combinations of the compounds of formula A and additional active therapeutic agents may be selected to treat patients infected with HCV and other conditions such as HIV infections. Accordingly, the compounds of formula A may be combined with one or more compounds useful in treating HIV, for example HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV.

More specifically, one or more compounds of the present invention may be combined with one or more compounds selected from the group consisting of:

1) HIV protease inhibitors, e.g., amprenavir, atazanavir, fosamprenavir, indinavir, lopinavir, ritonavir, lopinavir+ritonavir, nelfinavir, saquinavir, tipranavir, brecanavir, darunavir, TMC-126, TMC-114, mozenavir (DMP-450), JE-2147 (AG1776), AG1859, DG35, L-756423, 800334649, KNI-272, DPC-681, DPC-684, and GW640385X, DG17, PPL-100, 2) a HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirine), efavirenz, BILR 355 BS, VRX 840773, UK-453,061, RDEA806, 3) a HIV nucleoside inhibitor of reverse transcriptase, e.g., zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, fosalvudine tidoxil, apricitibine (AVX754), amdoxovir, KP-1461, abacavir+lamivudine, abacavir+lamivudine+zidovudine, zidovudine+lamivudine, 4) a HIV nucleotide inhibitor of reverse transcriptase, e.g., tenofovir, tenofovir disoproxil fumarate+emtricitabine, tenofovir disoproxil fumarate+emtricitabine+efavirenz, and adefovir, 5) a HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-707035, MK-2048, BA-011, BMS-538158, GSK364735C, 6) a gp41 inhibitor, e.g., enfuvirtide, sifuvirtide, FB006M, TRI-1144, SPC3, DES6, Locus gp41, CovX, and REP 9, 7) a CXCR4 inhibitor, e.g., AMD-070, 8) an entry inhibitor, e.g., SP01A, TNX-355, 9) a gp120 inhibitor, e.g., BMS-488043 and BlockAide/CR, 10) a G6PD and NADH-oxidase inhibitor, e.g., immunitin, 11) a CCR5 inhibitor, e.g., aplaviroc, vicriviroc, INCB9471, PRO-140, INCB15050, PF-232798, CCR5 mAb004, and maraviroc.

12) an interferon, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, and albuferon, 13) ribavirin analogs, e.g., rebetol, copegus, levovirin, VX-497, and viramidine (taribavirin)

14) NS5a inhibitors, e.g., A-831 and A-689,

15) NS5b polymerase inhibitors, e.g., NM-283, valopicitabine, R1626, PSI-6130 (R1656), HCV-796, BILB 1941, MK-0608, NM-107, R7128, VCH-759, PF-868554, GSK625433, and XTL-2125, 16) NS3 protease inhibitors, e.g., SCH-503034 (SCH-7), VX-950 (Telaprevir), ITMN-191, and BILN-2065, 17) alpha-glucosidase 1 inhibitors, e.g., MX-3253 (celgosivir) and UT-231B, 18) hepatoprotectants, e.g., IDN-6556, ME 3738, MitoQ, and LB-84451, 19) non-nucleoside inhibitors of HCV, e.g., benzimidazole derivatives, benzo-1,2,4-thiadiazine derivatives, and phenylalanine derivatives, 20) other drugs for treating HCV, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975 (isatoribine), XTL-6865, ANA 971, NOV-205, tarvacin, EHC-18, and NIM811, 21) pharmacokinetic enhancers, e.g., BAS-100 and SPI452, 22) RNAse H inhibitors, e.g., ODN-93 and ODN-112, 23) other anti-HIV agents, e.g., VGV-1, PA-457 (bevirimat), ampligen, HRG214, cytolin, polymun, VGX-410, KD247, AMZ 0026, CYT 99007, A-221 HIV, BAY 50-4798, MDX010 (iplimumab), PBS119, ALG889, and PA-1050040.

Exemplary Methods of Making the Compounds of the Invention.

The invention also relates to methods of making the compounds of the invention. The compounds are prepared by any of the applicable techniques of organic synthesis. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., *Advanced Organic Chemistry, Third Edition*, (John Wiley & Sons, New York, 1985), *Comprehensive Organic Synthesis. Selectivity, Strategy & Efficiency in Modern Organic Chemistry. In 9 Volumes*, Barry M. Trost, Editor-in-Chief (Pergamon Press, New York, 1993 printing).

A number of exemplary methods for the preparation of the compounds of the invention are provided below. These methods are intended to illustrate the nature of such preparations and are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g., inert gas environments) are common in the art and will be applied when applicable.

The terms "treated", "treating", "treatment", and the like, when used in connection with a chemical synthetic operation, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two. For example, treating indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis are used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Modifications of each of the exemplary schemes and in the examples (hereafter "exemplary schemes") leads to various analogs of the specific exemplary materials produce. The above-cited citations describing suitable methods of organic synthesis are applicable to such modifications.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g., an enantiomer, substantially free of its stereoisomer may be obtained by resolution of the racemic mixture using a method such as formation of diastereomers using optically active resolving agents (*Stereochemistry of Carbon Compounds*, (1962) by E. L. Eliel, McGraw Hill; Lochmuller, C. H., (1975) *J. Chromatogr.*, 113, 3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) *Stereochemistry of Organic Compounds*, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Hoye, T., WO 96/15111). By method (3), a racemic mixture of two enantiomers can be separated by chromatography using a chiral stationary phase (*Chiral Liquid Chromatography* (1989) W. J. Lough, Ed. Chapman and Hall, New York; Okamoto, (1990) *J. of Chromatogr.* 513:375-378). Enriched or purified enantiomers can be distinguished by methods used to distinguish other chiral molecules with asymmetric carbon atoms, such as optical rotation and circular dichroism.

SCHEMES AND EXAMPLES

General aspects of these exemplary methods are described below and in the Examples. Each of the products of the following processes is optionally separated, isolated, and/or purified prior to its use in subsequent processes.

A number of exemplary methods for the preparation of compounds of the invention are provided herein, for example, in the Examples herein below. These methods are intended to illustrate the nature of such preparations are not intended to limit the scope of applicable methods. Certain compounds of the invention can be used as intermediates for the preparation of other compounds of the invention.

HCV Assay Protocol

The anti-HCV activity of the compounds of this invention was tested in a human hepatoma Huh-7 cell line harboring a HCV replicon. The assay comprised the following steps:

Step 1: Compound Preparation and Serial Dilution.

Serial dilution was performed in 100% DMSO in a 384-well plate. A solution containing a compound at 225-fold concentration of the starting final serial dilution concentration was prepared in 100% DMSO and 15 uL added to the pre-specified wells in column 3 or 13 of a polypropylene 384-well plate. The rest of the 384-well plate was filled with 10 uL 100% DMSO except for columns 23 and 24, where 10 uL of 500 uM a HCV protease inhibitor (ITMN-191) in 100% DMSO was added. The HCV protease inhibitor was used a control of 100% inhibition of HCV replication. The plate was then placed on a Biomek FX Workstation to start the serial dilution. The serial dilution was performed for ten cycles of 3-fold dilution from column 3 to 12 or from column 13 to 22.

Step 2: Cell Culture Plate Preparation and Compound Addition

To each well of a black polypropylene 384-well plate, 90 μL of cell media containing 1600 suspended Huh-7 HCV replicon cells was added with a Biotek uFlow Workstation. A volume of 0.4 μL of the compound solution was transferred from the serial dilution plate to the cell culture plate on a Biomek FX Workstation. The DMSO concentration in the final assay condition was 0.44%. The plates were incubated for 3 days at 37° C. with 5% CO2 and 85% humidity.

Step 3: Detection of Cytotoxicity and Inhibition of Viral Replication a) Assessment of cytotoxicity: The media in the 384-well cell culture plate was aspirated with a Biotek EL405 plate-washer. A volume of 50 μL of a solution containing 400 nM Calcein AM in 100% PBS was added to each well of the plate with a Biotek uFlow Workstation. The plate was incubated for 30 minutes at room temperature before the fluorescence signal (emission 490 nm, exitation 520 nm) was measured with a Perkin Elmer Envision Plate Reader.

b) Assessment of inhibition of viral replication: The calcein-PBS solution in the 384-well cell culture plate was aspirated with a Biotek EL405 plate-washer. A volume of 20 μL of Dual-Glo luciferase buffer (Promega, Dual-Glo Luciferase Assay Reagent, cat. #E298B) was added to each well of the plate with a Biotek uFlow Workstation. The plate was incubated for 10 minutes at room temperature. A volume of 20 μL of a solution containing 1:100 mixture of Dual-Glo Stop & Glo substrate (Promega, Dual-Glo Luciferase Assay Reagent, cat. #E313B) and Dual-Glo Stop & Glo buffer (Promega, Dual-Glo Luciferase Assay Reagent, cat. #E314B) was then added to each well of the plate with a Biotek uFlow Workstation. The plate was incubated at room temperature for 10 minutes before the luminescence signal was measured with a Perkin Elmer Envision Plate Reader.

Step 4: Calculation

The percent cytotoxicity was determined by calcein AM conversion to fluorescent product. The average fluorescent signal from the DMSO control wells were defined as 100% nontoxic. The individual fluorescent signal from testing compound treated well was divided by the average signal from DMSO control wells and then multiplied by 100% to get the percent viability. The percent anti-HCV replication activity was determined by the luminescence signal from the testing well compared to DMSO controls wells. The background signal was determined by the average luminescence signal from the HCV protease inhibitor treated wells and was subtracted from the signal from the testing wells as well as the DMSO control wells. Following 3-fold serial dilutions, the $EC_{50}$ and $CC_{50}$ values were calculated by fitting % inhibition at each concentration to the following equation:

$$\% \text{ inhibition} = 100\% / [(EC_{50}/[I])^b + 1]$$

Where b is Hill's coefficient. See, for reference, Hill, A. V., *The Possible Effects of the Aggregation of the Molecules of Hæmoglobin on its Dissociation Curves*, J. Physiol. 40: iv-vii. (1910).

% inhibition values at any specific concentration, for example 10 μM, can also be derived from the formula above.

When tested, certain compounds of this invention were found to inhibit viral replication as listed in Table 1.

Compounds which are representative of the invention, along with their antiviral activities are listed in Table 1.

TABLE 1

| Compound | % inh at 10 uM (1B Replicon) |
| --- | --- |
|  | 99.61 |// structure
|  | 99.99 |
|  | 99.99 |
|  | 76.95 |

TABLE 1-continued
| Compound | % inh at 10 uM (1B Replicon) |
|---|---|
| 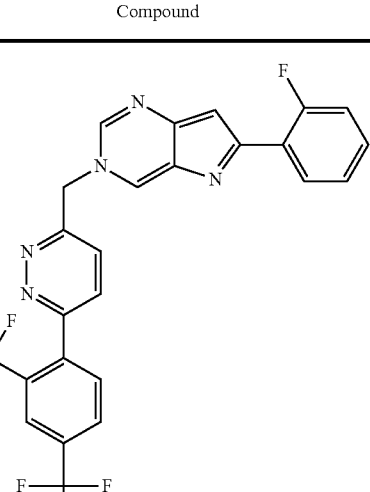 | 99.97 |
| | 98.06 |
| | 97.42 |
| | 99.97 |
| | 97.83 |
| | 99.98 |

TABLE 1-continued

| Compound | % inh at 10 uM (1B Replicon) |
|---|---|
| 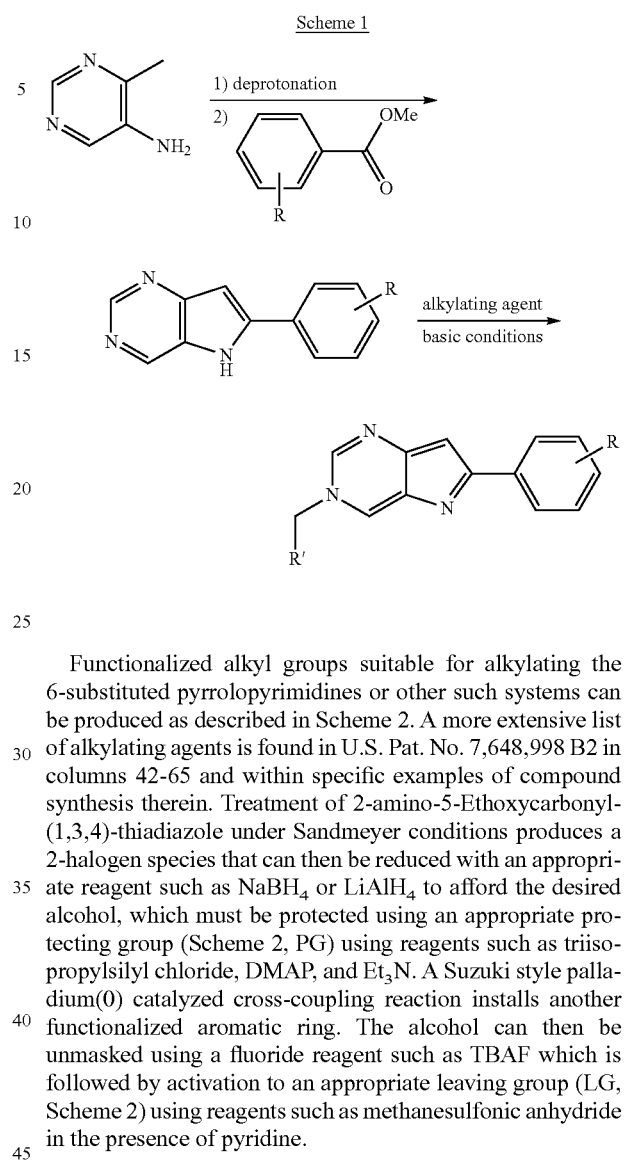 | 36.62 |
| | 99.92 |

SYNTHETIC EXAMPLES

Compounds included in the invention can be made using the general synthetic methods found in U.S. Pat. No. 7,648,998B2 which is hereby incorporated in its entirety by reference.

Compounds included in the invention can be made using several different strategies of organic synthesis. An example of one method is described in Scheme 1. An appropriate heteroaromatic compound such as 5-amino-4-methylpyrimidine can be deprotonated with a strong base such as n-butyl lithium to generate a di-anionic species that can then be treated with an appropriately functionalized carboxylic acid ester to undergo a cyclo-condensation reaction to form 6-substituted pyrrolopyrimidines. These can then be further alkylated using appropriately activated alkyl groups under basic conditions to produce compounds of formula (X).

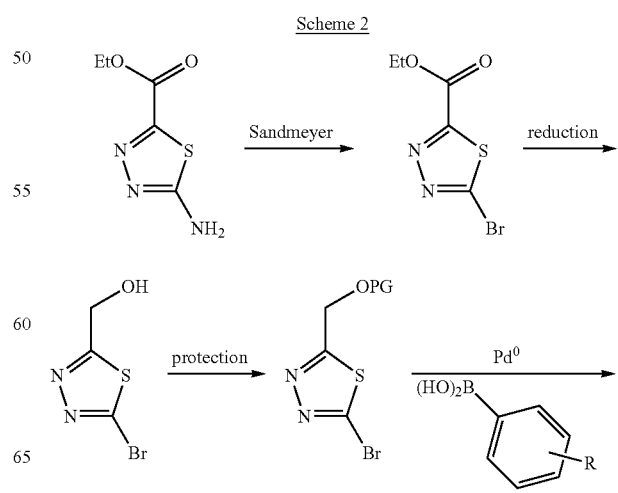

Functionalized alkyl groups suitable for alkylating the 6-substituted pyrrolopyrimidines or other such systems can be produced as described in Scheme 2. A more extensive list of alkylating agents is found in U.S. Pat. No. 7,648,998 B2 in columns 42-65 and within specific examples of compound synthesis therein. Treatment of 2-amino-5-Ethoxycarbonyl-(1,3,4)-thiadiazole under Sandmeyer conditions produces a 2-halogen species that can then be reduced with an appropriate reagent such as $NaBH_4$ or $LiAlH_4$ to afford the desired alcohol, which must be protected using an appropriate protecting group (Scheme 2, PG) using reagents such as triisopropylsilyl chloride, DMAP, and $Et_3N$. A Suzuki style palladium(0) catalyzed cross-coupling reaction installs another functionalized aromatic ring. The alcohol can then be unmasked using a fluoride reagent such as TBAF which is followed by activation to an appropriate leaving group (LG, Scheme 2) using reagents such as methanesulfonic anhydride in the presence of pyridine.

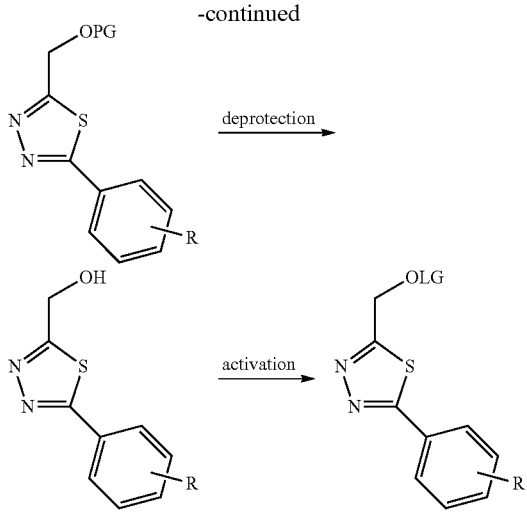

Two additional alkylating groups of interest are described in Example 6, p 70 of the U.S. Pat. No. 7,648,998 B2 (3-(2,4-Bis-trifluoromethyl-phenyl)-5-chloromethyl-isoxazole) and WO2008/005519 A2 (3-(2,4-Bis-trifluoromethyl-phenyl)-6-chloromethyl-pyridazine).

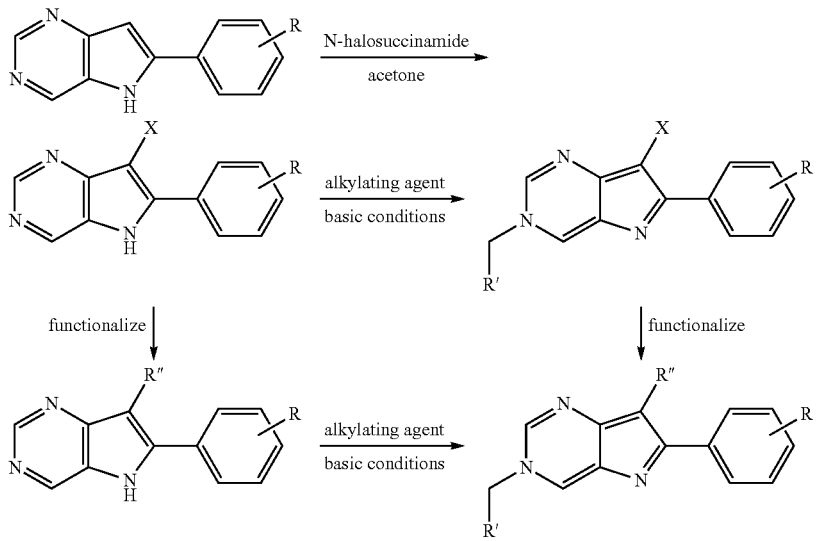

Scheme 3 describes synthetic strategies for installing additional functionality on the pyrrolopyrimidine portion of the compound. Treatment of the 6-substituted pyrrolopyrimidine, with a N-halosuccinamide reagent can install a halogen (preferably Br or I) in the 5-position. At this point, the halogenated system can be alkylated (R') using an appropriate reagent such as those described in Scheme 2. If desired, some functional groups can then be further altered (such as hydrolysis of cyano to carboxamide or carboxylic acid) to this point to produce additional compounds of formula (X).

Alternatively, the halogen can be replaced with additional functionality (R") prior to alkylation with R'. Examples of functionality such as cyano, carbonyl, and alkyl, aryl, or alkynyl groups can be installed using methods such as metal catalyzed cross-couplings or metalation followed by alkylation with appropriate electrophiles. These functionalized systems can then be alkylated with an appropriate alkylating reagent as described above.

Synthetic Examples 6-(2-fluorophenyl)-5H-pyrrolo[3,2-d]pyrimidine

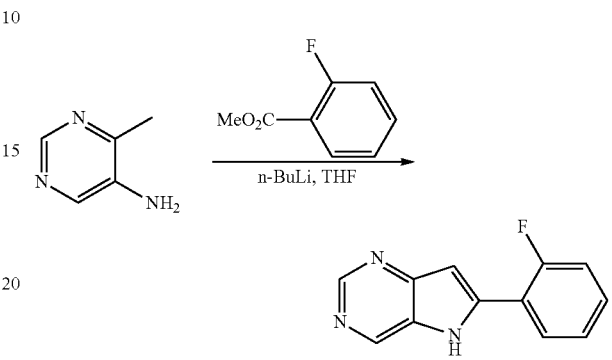

5-amino-4-methylpyrimidine (5 g, 45 mmol) was dissolved in 200 mL THF and cooled to −20° C. A solution of n-BuLi (112.5 mmol) was added over 10 minutes and the solution was kept at −20° C. for 30 min, then warmed to room temp and stirred for 3 h. It was then cooled to −40° C. and to it was added methyl-2-fluorobenzoate (1.75 mL, 13.7 mmol) and the solution stirred at −40° C. for 30 min and then warmed to room temp for 1 h. 50 mL of methanol was then added over 5 min, followed by 6N aq HCl. The solution was stirred for 18 h at room temp. It was then neutralized with $NaHCO_3$ to pH 8 and then diluted with ethyl acetate and water. The organics were washed with water three times and then brine and dried over sodium sulfate and concentrated in vacuo. The crude material was purified by flash chromatography using 10% methanol/DCM. 1.5 g of product was isolated as a yellow solid (16%). $^1$H-NMR: (d$_6$-DMSO, 400 MHz) δ 12.22 (s, 1H), 8.86 (s, 1H), 8.83 (s, 1H), 7.98(dt, 1H), 7.46 (m, 1H), 7.38 (m, 2H), 7.02(s, 1H) LC/MS: calculated for $C_{12}H_8FN_3$: 213.2; found 214.10 (M+H)$^+$.

6-(2-fluorophenyl)-7H-pyrrolo[2,3-c]pyridazine

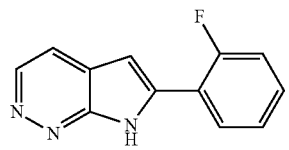 [SMILES: Fc1ccccc1-c1cc2ccnnc2[nH]1]

Prepared using procedure for 6-(2-fluorophenyl)-5H-pyrrolo[3,2-d]pyrimidine, substituting 3-amino-4-methylpyridazine (1 g, 9.16 mmol) for 5-amino-4-methyl-pyrimidine with appropriate adjustments to other reagents. 350 mg (18%) of the desired compound was obtained. $^1$H-NMR: (d$_6$-DMSO, 400 MHz) 12.80 (s, 1H), 8.86 (d, 1H), 8.07 (dt, 1H), 7.84 (d, 1H), 7.52 (m, 1H), 7.40 (m, 2H), 6.96 (d, 1H). LC/MS calculated for calculated for $C_{12}H_8FN_3$: 213.2; found 214.13 (M+H)$^+$.

7-Bromo-6-(2-fluorophenyl)-5H-pyrrolo[3,2-d]pyrimidine

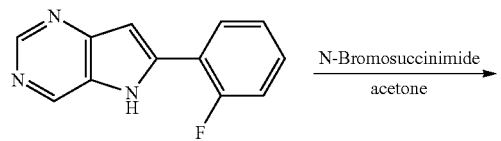

To a slurry of 6-(2-fluorophenyl)-5H-pyrrolo[3,2-d]pyrimidine (1.0 g) in acetone (50 mL) was added N-bromosuccinimide (1.0 g). The reaction was stirred at rt for 2 h, until complete conversion was observed by LC-MS. The reaction mixture was diluted with EtOAc (150 mL) and the solid was collected via filtration and washed with EtOAc yielding 820 mg of desired (60% yield). LCMS calculated for $C_{12}H_7BrFN_3$ 292.1, found 292.23: [M$^+$].

6-(2-fluorophenyl)-7-iodo-5H-pyrrolo[3,2-d]pyrimidine

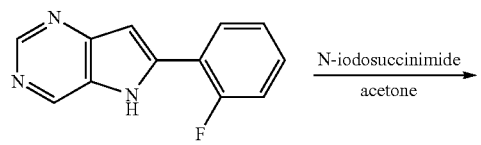

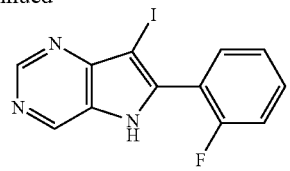

To a slurry of 6-(2-fluorophenyl)-5H-pyrrolo[3,2-d]pyrimidine (1.0 g) in acetone (25 mL) was added N-iodosuccinimide (1.4 g). The reaction was stirred at rt for 3 h, until complete conversion was observed by LC-MS. The reaction mixture was diluted with EtOAc (150 mL) and the solid was collected via filtration and washed with EtOAc yielding 1.23 g of desired (77% yield). LC-MS calculated for $C_{12}H_7FIN_3$: 339.1, found 339.96 [M$^+$].

6-(2-fluorophenyl)-5H-pyrrolo[3,2-d]pyrimidine-7-carbonitrile

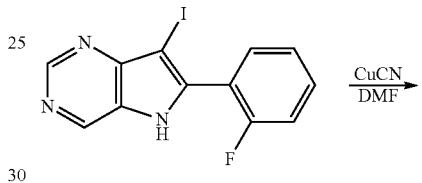

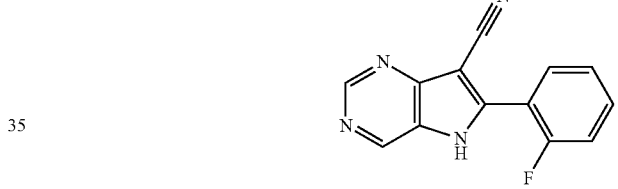

6-(2-fluorophenyl)-7-iodo-5H-pyrrolo[3,2-d]pyrimidine and CuCN in DMF were heated for 30 min at 175° C. in a microwave vial. The reaction mixture was filtered through a metal scavenging resin column, rinsed with DMF (~10 mL), and purified by HPLC (10-75% MeCN/H$_2$O with 1% formic acid) to give 29 mg of desired (17% yield). LC-MS calculated for $C_{13}H_7FN_4$: 238.2, found 239.09 [M+H]$^+$.

5-bromo-[1,3,4]thiadiazole-2-carboxylic acid ethyl ester

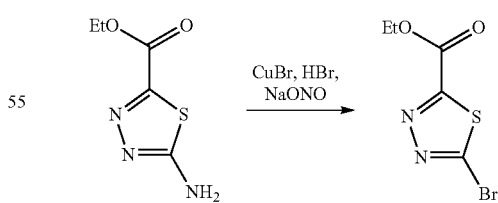

A 500 mL (three neck) round-bottom flask with a stir bar, needle inlet, and a gas outlet to a trap containing a 10% solution of Na$_2$S$_2$O$_3$ was charged with CuBr (1.24 g, 8.67 mmol, 0.1 equiv.) and HBr (48% aqueous solution, 108 mL). The purple solution was cooled to 3° C. (internal, ice bath), to which was added portion-wise a solid mixture of 5-amino-[1,3,4]thiadiazole-2-carboxylic acid ethyl ester (15.0 g, 86.6 mmol) and sodium nitrite (27.0 g, 391.3 mmol, 4.5 equiv.) over the course of 30 min. The reaction mixture was allowed to warm to room temperature for 2 h 15 min. The reaction mixture was diluted with CH₂Cl₂ and 10% aqueous Na₂S₂O₃ and the layers were separated. The aqueous layer was extracted 3 times with CH₂Cl₂. The combined organic layers were washed with Brine, dried over MgSO₄, and concentrated. The crude product was purified by column chromatography (ISCO XL, 330 g SiO₂ column, 20-25% EtOAc/Hexanes) to provide an off-white solid that was triturated with 5% EtOAc/Hexanes. Filtration provided 5-bromo-[1,3,4]thiadiazole-2-carboxylic acid ethyl ester (14.5 g, 71%) as white needles. Concentration and trituration of the mother liquor provided an additional product (2.3 g, 11%).

(5-Bromo-[1,3,4]thiadiazol-2-yl)-methanol

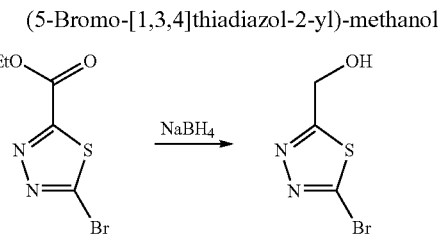

A 500 mL (two neck) round-bottom flask with a stir bar, gas inlet, and septum was charged with 5-bromo-[1,3,4]thiadiazole-2-carboxylic acid ethyl ester (8.91 g, 37.59 mmol), CH₂Cl₂ (100 mL), and methanol (50 mL). The solution was cooled to −74° C. (internal, acetone/CO₂ bath) and NaBH₄ (4.27 g, 112.8 mmol, 3 equiv.) was added slowly. The reaction mixture was allowed to warm to room temperature over 4 hours, during which time gas evolution was observed and the solution became yellow in color. The reaction mixture was diluted with EtOAc and washed with H₂O and Brine. The crude product was filtered through a SiO₂ plug (Yamazen, Large load column, 0-50% EtOAc/Hexanes). Recrystallization from TBME (~30 mL) provided (5-Bromo-[1,3,4]thiadiazol-2-yl)-methanol (4.22 g, 58%) as yellow needles. Concentration of the mother liquor and recrystallization from TBME provided additional product.

2-bromo-5-triisoproylsilanyloxymethyl-[1,3,4]thiadiazole

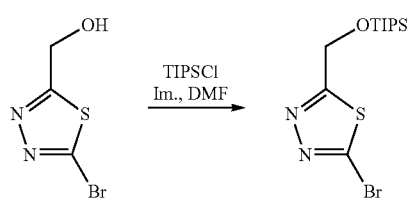

A 500 mL (one neck) round-bottom flask with a stir bar, septum and needle inlet was charged with (5-bromo-[1,3,4]thiadiazol-2-yl)-methanol (25 g, 128 mmol), DMF (250 mL), imidazole (17.9 g, 263 mmol, 2 equiv.) and TIPSCl (30.0 g, 155 mmol, 1.2 equiv.). The solution was stirred for 5 hours and diluted with EtOAc. The solution was washed with HCl (1N, 2×) and brine. The organic layer was dried over Na₂SO₄ and concentrated. The crude product was purified by silica gel chromatography (0-10% EtOAc/Hex) to provide 2-bromo-5-triisoproylsilanyloxymethyl-[1,3,4]thiadiazole (44.1 g, 98%).

2-(4-methoxy-2-trifluoromethyl-phenyl)-5-triisopropylsilanyloxymethyl-[1,3,4]thiadiazole

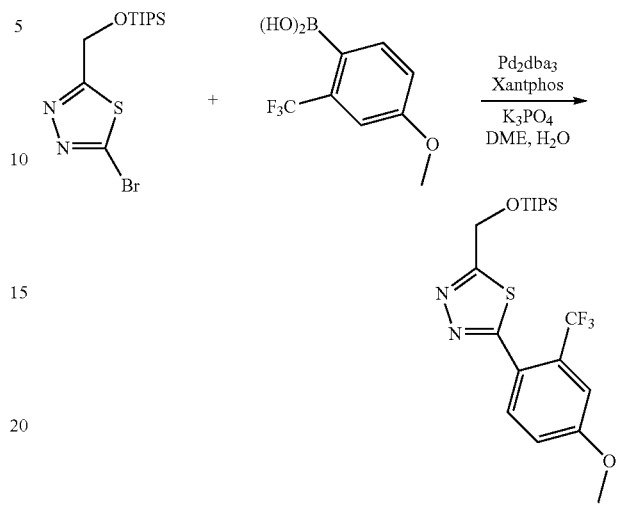

A 500 mL round-bottom flask with a stir bar, septum, and a needle inlet was charged with 4-methoxy-2-(trifluoromethyl)benzeneboronic acid (15.5 g, 70.6 mmol, 2 equiv.), DME (120 mL), 2-bromo-5-triisoproylsilanyloxymethyl-[1,3,4]thiadiazole (12.4 g, 35.3 mmol), and K₃PO₄ (2 M (aqueous), 37 mL, 74 mmol, 2.1 equiv.). The resulting solution was degassed with Ar for 30 min before Pd₂dba₃ (0.8 g, 1.76 mmol, 0.025 equiv.) and 4,5-bis(diphenylphosphino)-9,9-dimethylxanthene (Xantphos, 1 g, 3.52 mmol, 0.05 equiv.) were added. The resulting brown solution was heated to 80° C. (external, oil bath) for 3 h. The reaction was then cooled to room temperature, filtered through celite, and washed with EtOAc. The filtrate was then washed with H₂O and brine. The aqueous layers were extracted with EtOAc, and the combined organic layers were dried over Na₂SO₄ and concentrated. The resulting yellow oil was purified by silica gel chromatography (0-20% EtOAc/Hex) to give 2-(4-methoxy-2-trifluoromethyl-phenyl)-5-triisopropylsilanyl-oxymethyl-[1,3,4]thiadiazole as off-white solid (13.88 g, 88%). ¹H NMR (d₃-CDCl₃, 400 MHz) δ 7.61 (d, 1H), 7.33 (d, 1H), 7.14 (dd, 1H), 5.22 (s, 2H), 3.92 (s, 3H), 1.2 (m, 3H), 1.08 (s, 18H). LCMS: LCMS found 447.62 (M⁺+H, C₂₀H₂₉F₃N₂O₂SSi requires 446.60).

[5-(4-Methoxy-2-trifluoromethyl-phenyl)-[1,3,4]thiadiazol-2-yl]-methanol

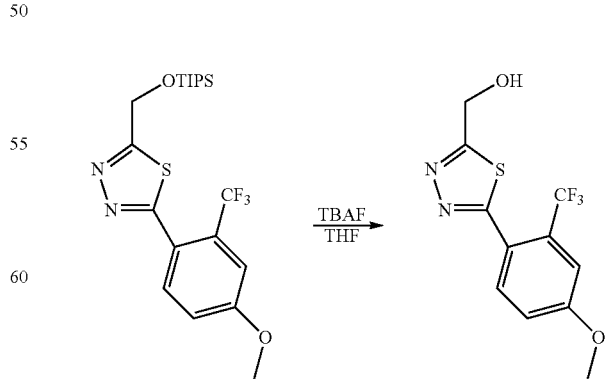

A 200 mL round-bottom flask with a stir bar, gas inlet, septum, and an addition funnel was charged with 2-(4-Methoxy-2-trifluoromethyl-phenyl)-5-triisopropyl-silanyloxymethyl-[1,3,4]thiadiazole (13.88, 31 mmol) and THF (62 mL). The solution was stirred at room temperature and TBAF (1 M in THF, 34 mL, 1.1 equiv.) was added dropwise. The reaction was allowed to stir at room temperature for 1 h before dilution with EtOAc. The solution was washed with H₂O and brine. The aqueous layers were backextracted with EtOAc. The combined organic layers were dried over Na₂SO₄, and concentrated. The crude oil was purified by silica gel chromatography (30-100% EtOAc/Hex) to provide [5-(4-Methoxy-2-trifluoromethyl-phenyl)-[1,3,4]thiadiazol-2-yl]-methanol as off-white solid (6.2 g, 69%). $^1$H NMR (d$_3$-CDCl$_3$, 400 MHz) δ 7.60 (d, 1H), 7.33 (d, 1H), 7.14 (dd, 1H), 5.15 (s, 2H), 3.92 (s, 3H). LC/MS found 291.11 (M$^+$+H, C$_{11}$H$_9$F$_3$N$_2$O$_2$S requires 290.26).

Methanesulfonic acid [5-(4-Methoxy-2-trifluoromethyl-phenyl)-[1,3,4]thiadiazol-2-yl]-methanyl ester

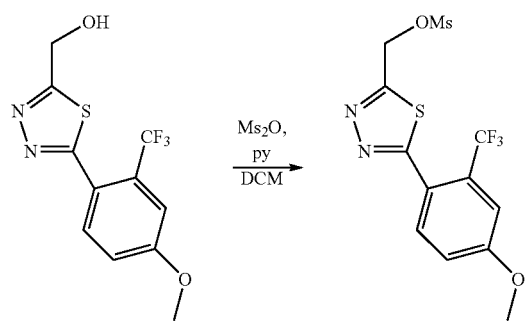

To a solution of 5-(4-Methoxy-2-trifluoromethyl-phenyl)-[1,3,4]thiadiazol-2-yl]-methanol (2.57 g, 8.85 mmol) in DCM (45 mL) was added methanesulfonic anhydride (1.91 g) followed by pyridine (1.2 mL) and the reaction was stirred at room temp for 1 h. The solid that crashed out was filtered off and the residue concentrated and purified by flash chromatography using 10-50% ethyl acetate/hexanes. Product containing fractions were pooled and concentrated and then recrystallized from hexanes/DCM to obtain the desired product. (2.87 g, 74%) LCMS: Found=369.2 (M$^+$+H), calculated: 368.21.

3-[5[(4-methoxy-2-trifluoromethyl-phenyl)-[1,3,4]thiadiazol-2-ylmethyl]-6-(2-fluoro-phenyl)-3H-pyrrolo[3,2-d]pyrimidine

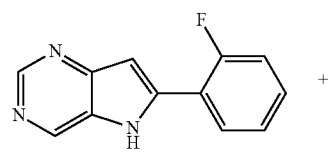

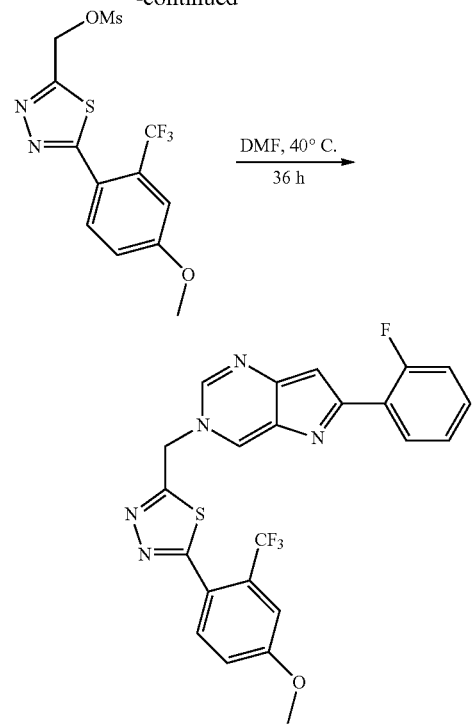

6-(2-Fluoro-phenyl)-5H-pyrrolo[3,2-d]pyrimidine (100 mg, 0.46 mmol) was dissolved in DMF (3 mL) and methanesulfonic acid [5-(4-Methoxy-2-trifluoromethyl-phenyl)-[1,3,4]thiadiazol-2-yl]-methyl ester (250 mg, 0.7 mmol) was added to it. The resulting solution was stirred at 40° C. for 36 h then cooled to room temp, filtered and purified by HPLC using 10-70% acetonitrile/water (+0.1% formic acid), followed by a repurification using 35-70% acetonitrile water (+0.1% formic acid). Product containing fractions were pooled and lyophilized to obtain 8.3 mg (4%) of the desired product. LCMS: Found=486.00, calculated: 485.09.

3-[5-(2,4-Bis-trifluoromethylphenyl)-[1,3,4]thiadiazol-2-ylmethyl]-6-(2-fluorophenyl)-3H-pyrrolo[3,2-d]pyrimidine

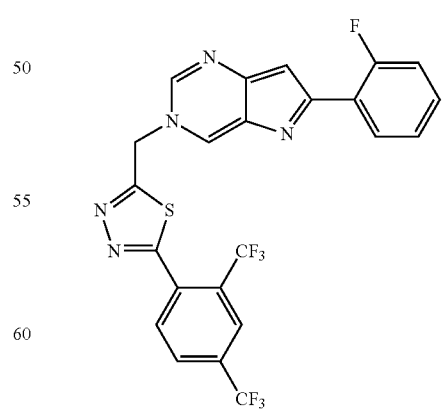

Prepared analogously to the method described for 3-[5[(4-methoxy-2-trifluoromethyl-phenyl)-[1,3,4]thiadiazol-2-ylmethyl]-6-(2-fluorophenyl)-3H-pyrrolo[3,2-d]pyrimidine beginning with 6-(2-fluorophenyl)-5H-pyrrolo[3,2-d]pyrimidine (200 mg, 0.93 mmol) and methanesulfonic acid [5-(2,4-bis-trifluoromethylphenyl)-[1,3,4]thiadiazol-2-yl]-methanyl ester (568 mg, 1.40 mmol) which produced 9 mg (5%) of the title compound. LCMS calculated for $C_{23}H_{12}F_7N_5S$: 523.4, found 524.01 (M+H)$^+$.

3-[3-(2,4-bis-trifluoromethylphenyl)-isoxazol-5-ylmethyl]-6-(2-fluoro-phenyl)-3H-pyrrolo[3,2-d]pyrimidine

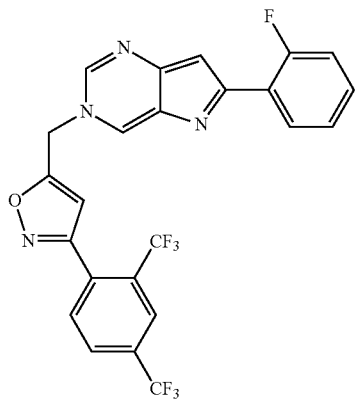 [SMILES: Fc1ccccc1-c1cc2ncn(Cc3cc(-c4ccc(C(F)(F)F)cc4C(F)(F)F)no3)cc-2n1]

Prepared analogously to the method described for 3-[5[(4-methoxy-2-trifluoromethyl-phenyl)-[1,3,4]thiadiazol-2-yl-methyl]-6-(2-fluorophenyl)-3H-pyrrolo[3,2-d]pyrimidine beginning with 6-(2-fluorophenyl)-5H-pyrrolo[3,2-d]pyrimidine (100 mg, 0.46 mmol) and toluene-4-sulfonic acid 3-(2,4-bis-trifluoromethylphenyl)-isoxazol-5-ylmethyl ester (322 mg, 0.7 mmol) to produce the desired product (16.1 mg, 7%). $^1$H-NMR: (d$_6$-DMSO, 400 MHz) δ 9.58 (s, 1H), 9.40 (s, 1H), 8.26 (s, 1H), 8.24 (d, 1H), 8.16 (dt, 1H), 7.83 (d, 1H), 7.72 (m, 1H), 7.58 (s, 1H), 7.52 (d, 1H), 7.44 (d, 1H) 7.13 (d, 1H), 6.20 (s, 2H). LCMS calculated for $C_{24}H_{13}F_7N_4O$ 506.4, found 507.09 (M+H)$^+$.

3-[6-(2,4-Bis-trifluoromethylphenyl)-pyridazin-3-ylmethyl]-6-(2-fluorophenyl)-3H-pyrrolo[3,2-d]pyrimidine

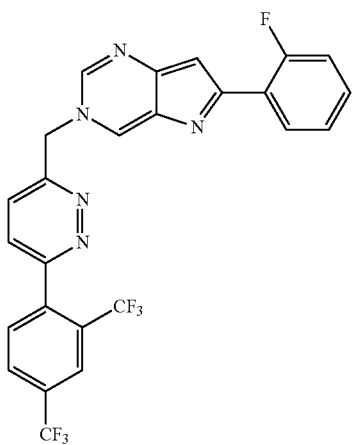 [SMILES: Fc1ccccc1-c1cc2ncn(Cc3ccc(-c4ccc(C(F)(F)F)cc4C(F)(F)F)nn3)cc-2n1]

Prepared analogously to the method described for 3-[5[(4-methoxy-2-trifluoromethyl-phenyl)-[1,3,4]thiadiazol-2-yl-methyl]-6-(2-fluorophenyl)-3H-pyrrolo[3,2-d]pyrimidine beginning with 6-(2-fluorophenyl)-5H-pyrrolo[3,2-d]pyrimidine (200 mg, 0.93 mmol) and 3-(2,4-Bis-trifluoromethylphenyl)-6-chloromethylpyridazine (383 mg, 1.12 mmol) to obtained desired product (9 mg, 5%).
$^1$H-NMR: (d$_6$-DMSO, 400 MHz) 8.58 (s, 1H), 8.55 (d, 1H), 8.45 (dt, 1H), 8.21 (s, 1H), 8.09 (d, 1H), 7.78 (m, 3H), 7.48 (m, 1H), 7.34-7.20 (m, 3H), 5.86 (s, 2H). LCMS: calculated for $C_{25}H_{14}F_7N_5$: 517.11, found 518.13 (M+H)$^+$.

2-[5[(4-methoxy-2-trifluoromethylphenyl)-[1,3,4]thiadiazol-2-ylmethyl]-6-(2-fluorophenyl)-2H-pyrrolo[2,3-c]pyridazine

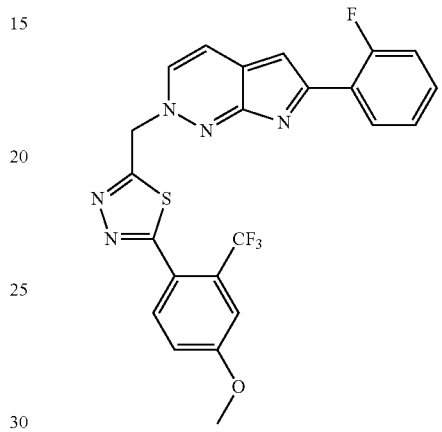

6-(2-Fluorophenyl)-7H-pyrrolo[2,3-c]pyridazine (50 mg, 0.234 mmol) was taken up in DMF (2 mL) and diisopropylethylamine (60 μL, 0.35 mmol) added to it, followed by methanesulfonic acid [5-(4-methoxy-2-trifluoromethylphenyl)-[1,3,4]thiadiazol-2-yl]-methyl ester (130 mg, 0.35 mmol). The reaction was stirred at room temp for 72 h and then purified by HPLC using 10-70% acetonitrile/water (+0.1% formic acid). Fractions containing desired product were pooled and lyophilized to produce 65 mg (57%).
$^1$H-NMR: (d$_6$-DMSO, 400 MHz) δ 8.76 (d, 1H), 8.42 (dt, 1H), 8.03 (d, 1H), 7.68 (d, 1H), 7.46 (m, 1H), 7.40 (d, 1H), 7.32 (m, 3H), 7.15 (d, 1H), 6.38 (s, 1H), 3.86 (s, 3H). LCMS calculated for $C_{23}H_{15}F_4N_5OS$ 485.09, found 486.08 (M+H)$^+$.

2-[3-(2,4-Bis-trifluoromethylphenyl)-isoxazol-5-ylmethyl]-6-(2-fluorophenyl)-2H-pyrrolo[2,3-c]pyridazine

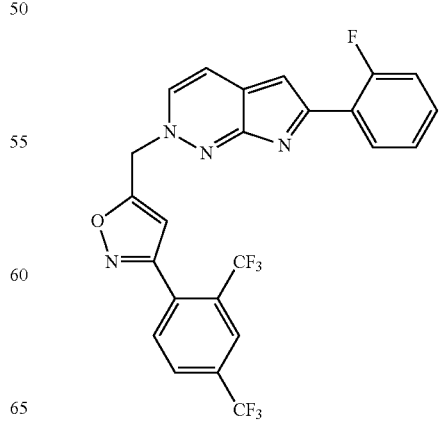

Prepared analogously to the method described for 2-[5[(4-methoxy-2-trifluoro-methylphenyl)-[1,3,4]thiadiazol-2-yl-methyl]-6-(2-fluorophenyl)-2H-pyrrolo[2,3-c]pyridazine beginning with 6-(2-fluorophenyl)-7H-pyrrolo[2,3-c]pyridazine (50 mg, 0.234 mmol) and toluene-4-sulfonic acid 3-(2,4-bis-trifluoromethylphenyl)-isoxazol-5-ylmethyl ester (164 mg, 0.35 mmol) to produce the titled product (25 mg, 21%). $^1$H-NMR: (d$_6$-DMSO, 400 MHz) δ 8.73 (d, 1H), 8.40 (dt, 1H), 8.21 (d, 1H), 8.16 (d, 1H), 8.04 (d, 2H), 7.93 (d, 1H), 7.48 (m, 1H), 7.32 (m, 2H), 7.14 (d, 1H), 7.00 (s, 1H), 6.15 (s, 2H). LCMS calculated for $C_{24}H_{13}F_7N_4O$ 506.10, found 507.07 (M+H)$^+$.

2-[6-(2,4-Bis-trifluoromethylphenyl)-pyridazin-3-ylmethyl]-6-(2-fluorophenyl)-2H-pyrrolo[2,3-c]pyridazine

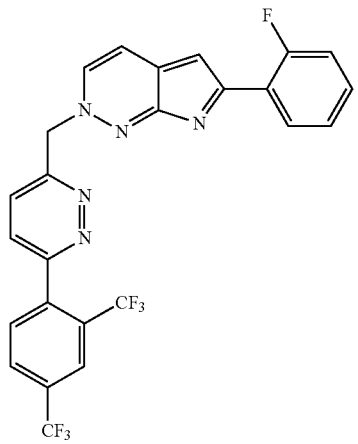 [SMILES: Fc1ccccc1-c1cc2ccn(Cc3ccc(-c4ccc(C(F)(F)F)cc4C(F)(F)F)nn3)nc-2n1]

Prepared analogously to the method described for 2-[5[(4-methoxy-2-trifluoro-methylphenyl)-[1,3,4]thiadiazol-2-yl-methyl]-6-(2-fluorophenyl)-2H-pyrrolo[2,3-c]pyridazine beginning with 6-(2-fluorophenyl)-7H-pyrrolo[2,3-c]pyridazine (50 mg, 0.234 mmol) and 3-(2,4-Bis-trifluoromethylphenyl)-6-chloromethylpyridazine (95 mg, 0.27 mmol) to produce the titled compound (21.6 mg, 18%). $^1$H-NMR: (d$_6$-DMSO, 400 MHz) δ 8.78 (d, 1H), 8.38 (dt, 1H), 8.21 (d, 2H), 8.02 (d, 1H), 7.95 (d, 1H), 7.89 (d, 1H), 7.86 (d, 1H), 7.47 (m, 1H), 7.31 (m, 2H), 7.12 (d, 1H), 6.22 (s, 2H). LCMS calculated for $C_{25}H_{14}F_7N_5$: 517.11, found 518.15 (M+H)$^+$.

7-Bromo-6-(2-fluorophenyl)-3-[5-(4-methoxy-2-trifluoromethylphenyl)-[1,3,4]thiadiazol-2-ylmethyl]-3H-pyrrolo[3,2-d]pyrimidine

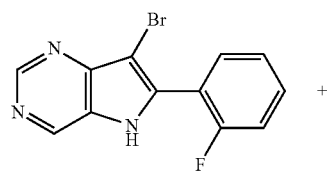

+

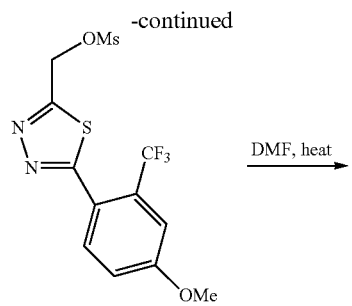

$\xrightarrow{\text{DMF, heat}}$

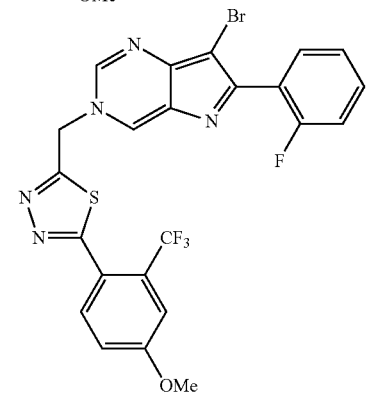

A solution of 7-bromo-6-(2-fluorophenyl)-5H-pyrrolo[3,2-d]pyrimidine (152 mg, 0.52 mmol) and methanesulfonic acid 5-(4-methoxy-2-trifluoromethylphenyl)-[1,3,4]thiadiazol-2-ylmethyl ester (211 mg, 0.57 mmol) were stirred in 2 mL DMF at 65° C. for 14 h. The solution was then heated to 85° C. for 4 h and cooled to rt. The resulting solution was filtered and purified by HPLC (10-70% MeCN/H$_2$O with 1% formic acid). Lyophilization of the pure fractions gave 103 mg (0.183 mmol, 35% yield) of the titled compound. $^1$H NMR (DMSO-d$_6$): 9.15 (s, 1H), 8.96 (s, 1H), 7.72 (d, 1H), 7.64 (t, 1H), 7.55 (q, 1H), 7.43 (s, 1H), 7.32-7.42 (m, 3H), 6.23 (s, 2H), 3.92 (s, 3H). LC-MS calculated for $C_{23}H_{14}BrF_4N_5OS$ 563.00, found 564.35 [M+H]$^+$.

6-(2-fluorophenyl)-3-[5-(4-methoxy-2-trifluoromethylphenyl)-[1,3,4]thiadiazol-2-ylmethyl]-3H-pyrrolo[3,2-d]pyrimidine-7-carbonitrile

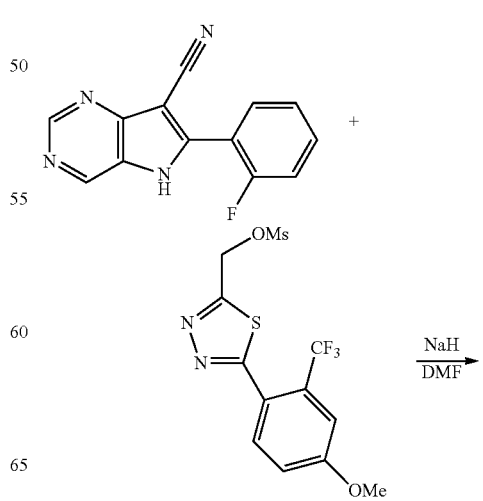

-continued

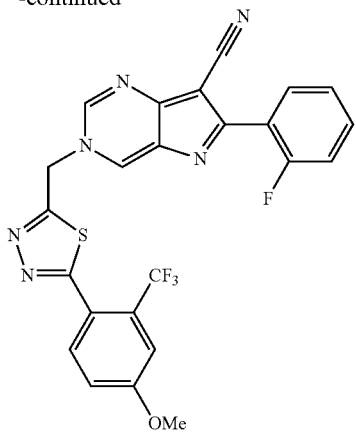

To a solution of 6-(2-fluorophenyl)-5H-pyrrolo[3,2-d]pyrimidine-7-carbonitrile (29 mg) and methanesulfonic acid 5-(4-methoxy-2-trifluoromethylphenyl)-[1,3,4]thiadiazol-2-ylmethyl ester (49 mg) in DMF was added NaH (5 mg). The reaction was stirred for 14 h at rt. The reaction was quenched by slow addition of AcOH (glacial), filtered, and purified by HPLC (10-70% MeCN/H$_2$O with 1% formic acid) then lyophilized to give 5.3 mg of the titled compound (8%). $^1$H NMR (DMSO-d$_6$): 9.40 (s, 1 h), 9.18 (s, 1 h), 7.85 (t, 1 h), 7.73 (d, 1H), 7.56-7.64 (m, 1H), 7.35-7.47 (m, 4H), 6.30 (s, 2H), 3.93 (s, 3H). LC-MS calculated for C$_{24}$H$_{14}$F$_4$N$_6$OS 510.5, found 511.00 [M+H]$^+$.

6-(2-fluorophenyl)-3-[5-(4-methoxy-2-trifluoromethylphenyl)-[1,3,4]thiadiazol-2-ylmethyl]-3H-pyrrolo[3,2-]pyrimidine-7-carboxylic acid amide

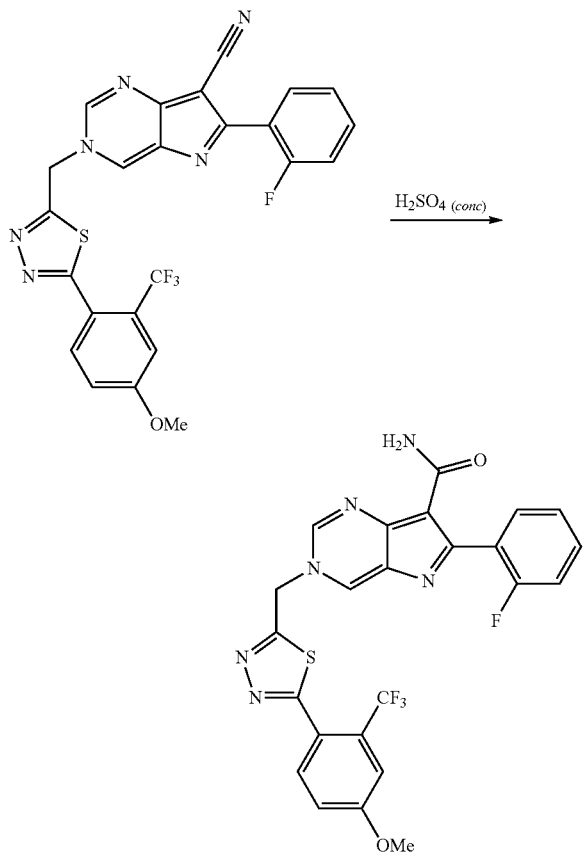

A solution of 6-(2-fluorophenyl)-3-[5-(4-methoxy-2-trifluoromethylphenyl)-[1,3,4]thiadiazol-2-ylmethyl]-3H-pyrrolo[3,2-d]pyrimidine-7-carbonitrile (12 mg) in cone. H$_2$SO$_4$ (0.5 mL) was stirred at rt for 18 h. The sulfuric acid was removed in vacuo, the residue was dissolved in DMF and purified via HPLC (10-60% MeCN/H$_2$O with 1% formic acid) then lyophilized to give the titled compound (2.2 mg, 18% yield).

We claim:
1. A compound of formula (A)

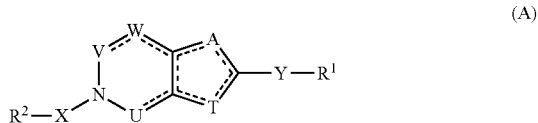

(A)

wherein:
the dotted lines represent optional double bonds, provided that no two double bonds are adjacent to one another, and that the dotted lines together represent 3 or 4 double bonds;
U is N or CR$^3$, T is N or CR$^4$, A is N or CR$^5$, W is N or CR$^6$, V is N or CR$^7$;
At least one of U, V or W is N; and
At least one of A and T is not N;
X is selected from the group consisting of C$_1$-C$_{10}$ alkylene, C$_{2-10}$ alkenylene and C$_{2-10}$ alkynylene, wherein each of said C$_1$-C$_{10}$ alkylene, C$_{2-10}$ alkenylene and C$_{2-10}$ alkynylene may have one or more carbon atoms replaced by a heteroatom selected from O, S, or N and wherein each of said C$_1$-C$_{10}$ alkylene, C$_{2-10}$ alkenylene or C$_{2-10}$ alkynylene and heteroatom may be optionally substituted with 1 or more R$^{20}$;
Y is selected from the group consisting of a single bond, O, S(O)$_m$, NR$^{11}$, C$_{1-10}$ alkylene, C$_{2-10}$ alkenylene and C$_{2-10}$ alkynylene, wherein each of said C$_{1-10}$ alkylene, C$_{2-10}$ alkenylene and C$_{2-10}$ alkynylene may have one or more carbon atoms replaced by a heteroatom selected from O, S, and N;
R$^1$ is selected from the group consisting of hydrogen, aryl, heterocycle, C$_1$-C$_{10}$ alkoxy, C$_1$-C$_{10}$ thioalkyl, C$_1$-C$_{10}$ alkylamino, C$_1$-C$_{10}$ dialkylamino, C$_3$-C$_{10}$ cycloalkyl, and C$_4$-C$_{10}$ cycloalkenyl, wherein each of said aryl, heterocycle, C$_1$-C$_{10}$ alkoxy, C$_1$-C$_{10}$ thioalkyl, C$_1$-C$_{10}$ alkylamino, C$_1$-C$_{10}$ dialkylamino, C$_3$-C$_{10}$ cycloalkyl, and C$_4$-C$_{10}$ cycloalkenyl may be optionally substituted with 1 or more R$^{20}$;
R$^2$ is selected from the group consisting of aryl, aryloxy, arylthio, cycloalkyl, cycloalkenyl, alkynyl and heterocycle, wherein each of said aryl, aryloxy, arylthio, cycloalkyl, cycloalkenyl, alkynyl and heterocycle may be optionally substituted with one or more R$^{17}$;
R$^3$ and R$^7$ are independently selected from the group consisting of hydrogen, C$_{1-18}$ alkyl, C$_{2-18}$ alkenyl, C$_{2-18}$ alkynyl, C$_{1-18}$ alkoxy, S(O)$_m$R$^9$, halogen, —CN, —NO$_2$, —NR$^{13}$R$^{14}$, haloalkyloxy, haloalkyl, —C(=O)R$^9$, —C(=O)OR$^9$, —C(=S)R$^9$, SH, aryl, aryloxy, arylthio, arylalkyl, C$_{1-18}$ hydroxyalkyl, C$_{3-10}$ cycloalkyl, C$_{3-10}$ cycloalkyloxy, C$_{3-10}$ cycloalkylthio, C$_{3-10}$ cycloalkenyl, (=O), (=S), =NR$^{21}$ and heterocycle, wherein any alkyl, cycloalkyl, alkenyl, aryl and heterocycle may be optionally substituted with 1 or more R$^{20}$;
R$^4$, R$^5$ and R$^6$ are independently selected from the group consisting of hydrogen, C$_{1-18}$ alkyl, C$_{2-18}$ alkenyl, C$_{2-18}$ alkynyl, $C_{1-18}$ alkoxy, $S(O)_mR^9$, halogen, —OH, —CN, —NO$_2$, —NR$^{13}$R$^{14}$, haloalkyloxy, haloalkyl, —C(=O)R$^9$, —C(=S)R$^9$, SH, aryl, aryloxy, arylthio, arylalkyl, $C_{1-18}$ hydroxyalkyl, $C_{3-10}$ cycloalkyl, $C_{3-10}$ cycloalkyloxy, $C_{3-10}$ cycloalkylthio, $C_{3-10}$ cycloalkenyl, and heterocycle, wherein each of said alkyl, cycloalkyl, alkenyl, aryl and heterocycle may be optionally substituted with 1 or more $R^{20}$;

$R^9$ and $R^{18}$ are independently selected from the group consisting of hydrogen, OH, $C_{1-18}$ alkyl, $C_{2-18}$ alkenyl, $C_{3-10}$ cycloalkyl, $C_{4-10}$ cycloalkenyl, $C_{1-18}$ alkoxy, —NR$^{15}$R$^{16}$, aryl, CH$_2$OCH(=O)R$^{9a}$, and CH$_2$C(=O)OR$^{9a}$ where $R^{9a}$ is $C_1$-$C_{12}$ alkyl, $C_6$-$C_{20}$ aryl, $C_6$-$C_{20}$ alkylaryl or $C_6$-$C_{20}$ aralkyl;

$R^{11}$ is selected from the group consisting of hydrogen, $C_{1-18}$ alkyl, $C_{2-18}$ alkenyl, $C_{3-10}$ cycloalkyl, $C_{4-10}$ cycloalkenyl, aryl, —C(=O)R$^{12}$, and heterocycle;

$R^{12}$ is selected from the group consisting of hydrogen, $C_{1-18}$ alkyl, $C_{2-18}$ alkenyl, aryl, $C_{3-10}$ cycloalkyl, and $C_{4-10}$ cycloalkenyl;

$R^{13}$ and $R^{14}$ are independently selected from the group consisting of $C_{1-18}$ alkyl, $C_{2-18}$ alkenyl, aryl, $C_{2-18}$ alkynyl, $C_{3-10}$ cycloalkyl, $C_{4-10}$ cycloalkenyl, heterocycle, —C(=O)R$^{12}$; $S(O)_mR^9$ and —C(=S)R$^{12}$, or $R^{13}$ and $R^{14}$ together with the nitrogen to which they are attached form a heterocycle;

$R^{15}$ and $R^{16}$ are independently selected from the group consisting of hydrogen, $C_{1-18}$ alkyl, $C_{2-18}$ alkenyl, $C_{2-18}$ alkynyl, aryl, $C_{3-10}$ cycloalkyl, $C_{4-10}$ cycloalkenyl and an amino acid residue;

$R^{17}$ is selected from the group consisting of hydrogen, $C_{1-18}$ alkyl, $C_{2-18}$ alkenyl, $C_{2-18}$ alkynyl, $C_{1-18}$ alkoxy, $C_{1-18}$ alkylthio, $C_{1-18}$ alkylsulfoxide, $C_{1-18}$ alkylsulfone, $C_{1-18}$ halogenated alkyl, $C_{2-18}$ halogenated alkenyl, $C_{2-18}$ halogenated alkynyl, $C_{1-18}$ halogenated alkoxy, $C_{1-18}$ halogenated alkylthio, $C_{3-10}$ cycloalkyl, $C_{3-10}$ cycloalkenyl, halogen, OH, CN, CO$_2$H, CO$_2$R$^{18}$, NO$_2$, NR$^{13}$R$^{14}$, haloalkyl, C(=O)R$^{18}$, C(=S)R$^{18}$, SH, aryl, aryloxy, arylthio, arylsulfoxide, arylsulfone, arylsulfonamide, arylalkyl, arylalkyloxy, arylalkylthio, heterocycle and $C_{1-18}$ hydroxyalkyl, where each of said aryl, aryloxy, arylthio, arylsulfoxide, arylsulfone, arylsulfonamide, arylalkyl, arylalkyloxy, arylalkylthio, heterocycle and $C_{1-18}$ hydroxyalkyl may be optionally substituted with 1 or more $R^{19}$;

$R^{19}$ is selected from the group consisting of hydrogen, $C_{1-18}$ alkyl, $C_{2-18}$ alkenyl, $C_{2-18}$ alkynyl, $C_{1-18}$ alkoxy, $C_{2-18}$ alkenyloxy, $C_{2-18}$ alkynyloxy, $C_{1-18}$ alkylthio, $C_{3-10}$ cycloalkyl, $C_{4-10}$ cycloalkenyl, halogen, —OH, —CN, cyanoalkyl, —NO$_2$, —NR$^{13}$R$^{14}$, $C_{1-18}$ haloalkyl, $C_{1-18}$ haloalkoxy, —C(=O)R$^{18}$, —C(=O)OR$^{18}$, —OalkenylC(=O)OR$^{18}$, —OalkylC(=O)NR$^{15}$R$^{16}$, —OalkylOC(=O)R$^{18}$, —C(=S)R$^{18}$, SH, —C(=O)N($C_{1-6}$ alkyl), —N(H)S(O)(O)($C_{1-6}$ alkyl), aryl, heterocycle, $C_{1-18}$ alkylsulfone, arylsulfoxide, arylsulfonamide, aryl($C_{1-18}$)alkyloxy, aryloxy, aryl($C_{1-18}$alkyl)oxy, arylthio, aryl($C_{1-18}$)alkylthio and aryl($C_{1-18}$)alkyl, wherein aryl, heterocycle, $C_{1-18}$alkylsulfone, arylsulfoxide, arylsulfonamide, aryl($C_{1-18}$)alkyloxy, aryloxy, aryl($C_{1-18}$alkyl)oxy, arylthio, aryl($C_{1-18}$)alkylthio and aryl($C_{1-18}$)alkyl may be optionally substituted with 1 or more $R^{20}$;

$R^{20}$ is selected from the group consisting of hydrogen, $C_{1-18}$ alkyl, $C_{2-18}$ alkenyl, $C_{2-18}$ alkynyl, heterocycle, $C_{1-18}$ alkoxy, $C_{1-18}$ alkylthio, $C_{1-18}$ alkylsulfoxide, $C_{1-18}$ alkylsulfone, $C_{1-18}$ halo-alkyl, $C_{2-18}$ halo-alkenyl, $C_{2-18}$ halo-alkynyl, $C_{1-18}$ halo-alkoxy, $C_{1-18}$ halo-alkylthio, $C_{3-10}$ cycloalkyl, $C_{3-10}$ cycloalkenyl, halogen, OH, CN, oxo, cyanoalkyl, —CO$_2$R$^{18}$, NO$_2$, —NR$^{13}$R$^{14}$, $C_{1-18}$ haloalkyl, C(=O)R$^{18}$, C(=S)R$^{18}$, SH, aryl, aryloxy, arylthio, arylsulfoxide, arylsulfone, arylsulfonamide, aryl($C_{1-18}$)alkyl, aryl($C_{1-18}$)alkyloxy, aryl($C_{1-18}$)alkylthio and $C_{1-18}$ hydroxyalkyl;

$R^{21}$ is selected from the group consisting of hydrogen, $C_{1-18}$ alkyl, $C_{3-10}$ cycloalkyl, $C_{1-18}$ alkoxy, ($C_{3-10}$ cycloalkyl)-$C_{1-6}$alkyl, aryl and aryl$C_{1-18}$ alkyl;

m is an integer from 0 to 2;

and the pharmaceutically acceptable salts thereof.

2. The compound of claim 1 wherein either, but not both A or T is N.

3. The compound of claim 2 which is a compound of formula A1 wherein all other substituents are as defined as for compounds of formula A:

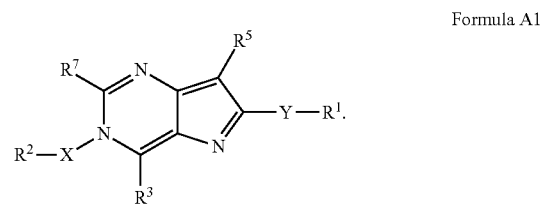

Formula A1

4. The compound of claim 2 which is a compound of formula A2 wherein all other substituents are as defined as for compounds of formula A:

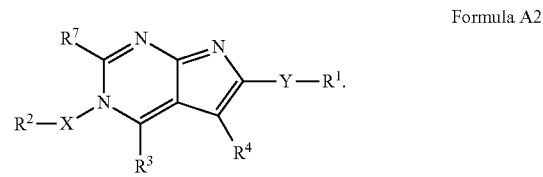

Formula A2

5. The compound of claim 2 which is a compound of formula A3 wherein all other substituents are as defined as for compounds of formula A:

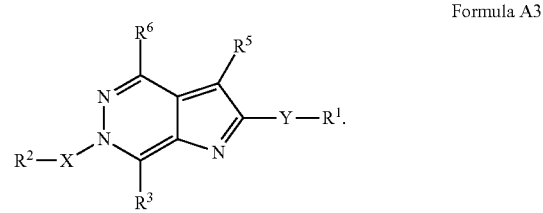

Formula A3

6. The compound of claim 2 which is a compound of formula A4 wherein all other substituents are as defined as for compounds of formula A:

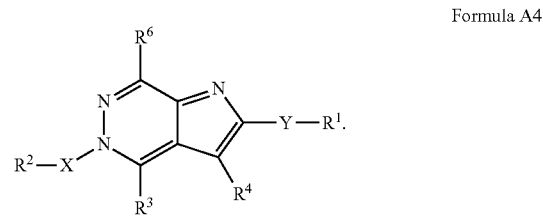

Formula A4

7. The compound of claim 2 which is a compound of formula A5 wherein all other substituents are as defined as for compounds of formula A:

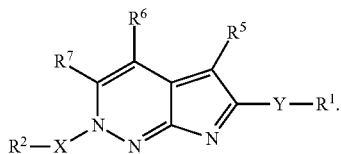

Formula A5

8. The compound of claim 2 which is a compound of formula A6 wherein all other substituents are as defined as for compounds of formula A:

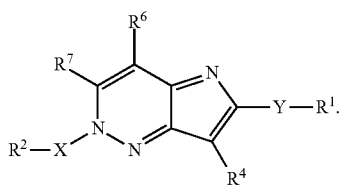

Formula A6

9. The compound of claim 2 which is a compound of formula A7 wherein all other substituents are as defined as for compounds of formula A:

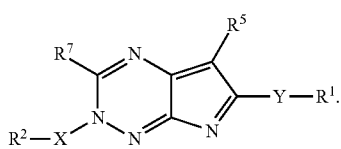

Formula A7

10. The compound of claim 2 which is a compound of formula A8 wherein all other substituents are as defined as for compounds of formula A:

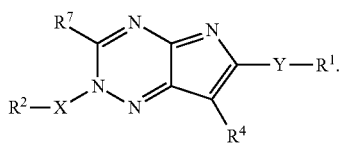

Formula A8

11. The compound of claim 1 wherein $R^7$ is H.
12. The compound of claim 1 wherein $R^4$ or $R^5$ is H.
13. The compound of claim 1 wherein Y is a bond.
14. The compound of claim 1 wherein $R^1$ is aryl or heterocycle, wherein each of said aryl or heterocycle may be optionally substituted with 1 or more $R^{20}$.
15. The compound of claim 14 wherein $R^{20}$ is selected from the group consisting of hydrogen, $C_{1-18}$ alkyl, $C_{2-18}$ alkenyl, $C_{2-18}$ alkynyl, $C_{1-18}$ alkoxy, $C_{1-18}$ alkylthio, $C_{1-18}$ alkylsulfoxide, $C_{1-18}$ alkylsulfone, $C_{1-18}$ halo-alkyl, $C_{2-18}$ halo-alkenyl, $C_{2-18}$ halo-alkynyl, $C_{1-18}$ halo-alkoxy, $C_{1-18}$ halo-alkylthio, $C_{3-10}$ cycloalkyl, $C_{3-10}$ cycloalkenyl, halogen, CN, oxo, cyanoalkyl, $C_{1-18}$ haloalkyl, $C(=O)R^{18}$, $C(=S)R^{18}$, and $C_{1-18}$ hydroxyalkyl.
16. The compound of claim 1 wherein $R^1$ is phenyl wherein the phenyl is optionally substituted with 1 or more substituents selected from the group consisting of halogen and $C_1$ to $C_5$ alkyl.

17. The compound of claim 1 wherein X is methylene wherein the methylene may be optionally substituted with 1 or more $R^{20}$.
18. The compound of claim 17 wherein $R^{20}$ is selected from the group consisting of hydrogen, $C_{1-18}$ alkyl, $C_{2-18}$ alkenyl, $C_{2-18}$ alkynyl, halogen, OH, CN, cyanoalkyl and $C_{1-18}$ haloalkyl.
19. The compound of claim 1 wherein X is methylene.
20. The compound of claim 1 wherein $R^2$ is selected from the group consisting of aryl and heterocycle wherein aryl and heterocycle may be optionally substituted with 1 or more $R^{17}$.
21. The compound of claim 20 wherein $R^2$ is selected from the group consisting of

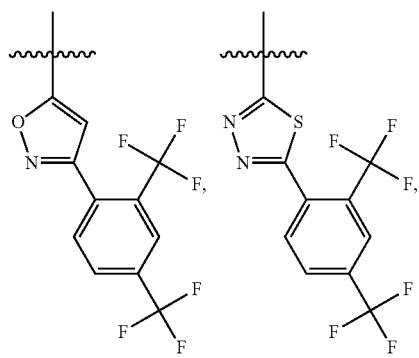

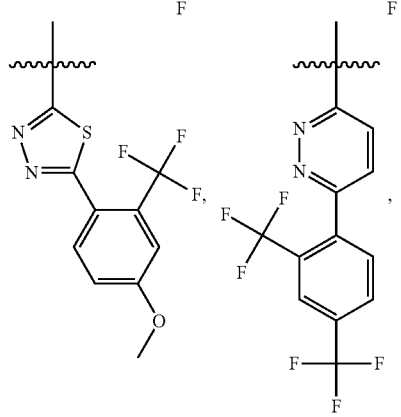

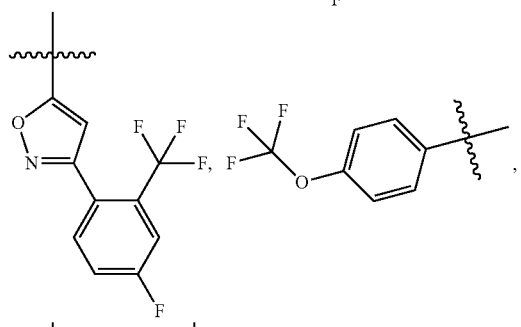

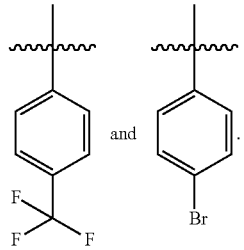

22. The compound of claim 1 selected from the group consisting of

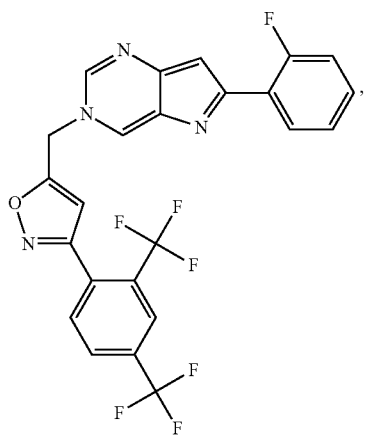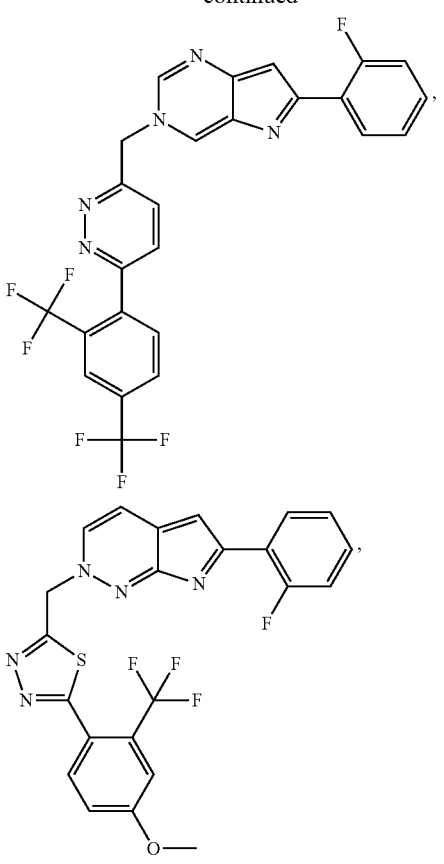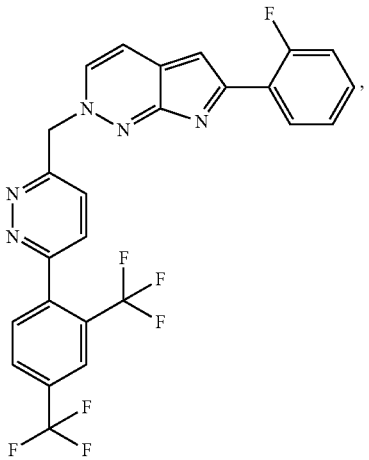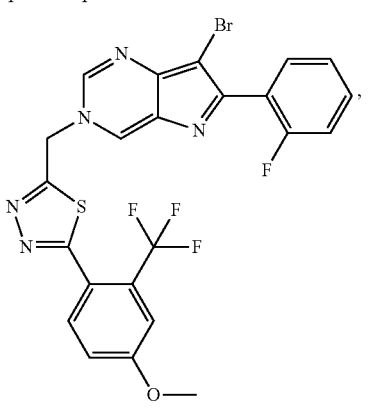

-continued

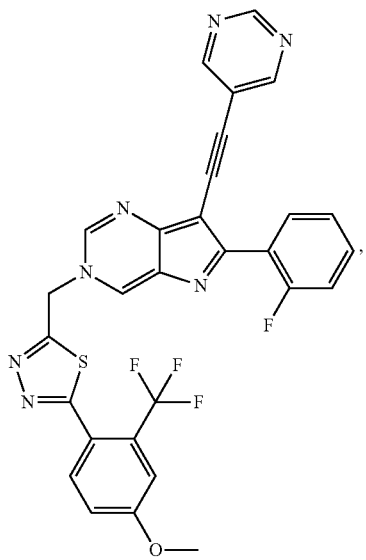

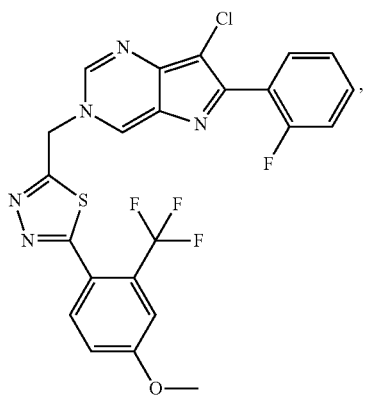

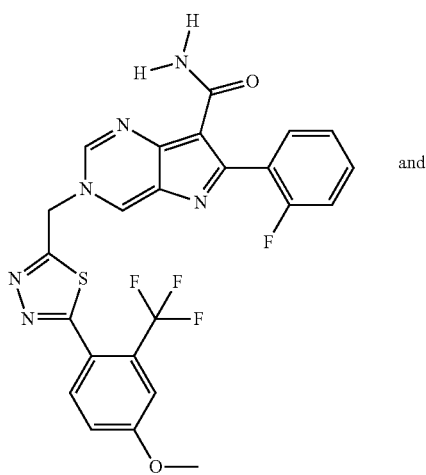

-continued

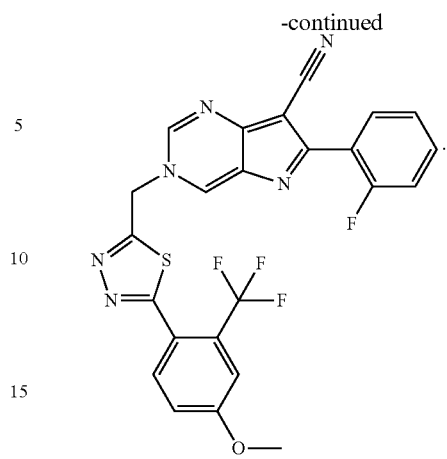

23. A compound of formula A10

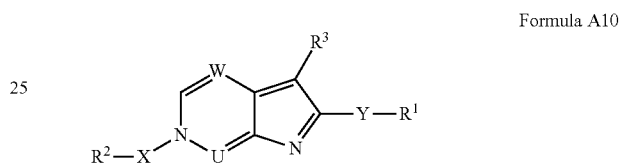

Formula A10 wherein:
one of U or W is N, and the other U or W is CH;
X is $C_1$-$C_6$ alkylene;
Y is a single bond;
$R^1$ is phenyl optionally substituted with one to three $R^{20}$;
$R^2$ is heterocycle optionally substituted with one to three $R^{17}$;
$R^3$ is hydrogen, $C_{1-6}$ alkyl, $C_{2-6}$ alkenyl, $C_{2-6}$ alkynyl, $C_{1-6}$ alkoxy, $S(O)_mR^9$, halogen, —OH, —CN, —NO$_2$, —NR$^{13}$R$^{14}$, —C(=O)R$^9$, —C(=O)OR$^9$, —C(=S)R$^9$, and SH, wherein any alkyl and alkenyl may be optionally substituted with one to three $R^{20}$;
$R^9$ and $R^{18}$ are independently selected from the group consisting of hydrogen, $C_{1-6}$ alkyl, $C_{2-6}$ alkenyl, $C_{1-6}$ alkoxy, and —NR$^{15}$R$^{16}$;
$R^{13}$ and $R^{14}$ are independently selected from the group consisting of hydrogen, and $C_{1-6}$ alkyl;
$R^{15}$ and $R^{16}$ are independently selected from the group consisting of hydrogen, $C_{1-6}$ alkyl, and an amino acid residue;
$R^{17}$ is phenyl optionally substituted with one to three $R^{19}$;
$R^{19}$ is selected from the group consisting of hydrogen, $C_{1-18}$ alkyl, $C_{2-18}$ alkenyl, $C_{2-18}$ alkynyl, $C_{1-18}$ alkoxy, $C_{2-18}$ alkenyloxy, $C_{2-18}$ alkynyloxy, $C_{1-18}$ alkylthio, $C_{3-10}$ cycloalkyl, $C_{4-10}$ cycloalkenyl, halogen, —OH, —CN, cyanoalkyl, —NO$_2$, —NR$^{13}$R$^{14}$, $C_{1-18}$ haloalkyl, $C_{1-18}$ haloalkoxy, —C(=O)R$^{18}$, —C(=O)OR$^{18}$, —OalkenylC(=O)OR$^{18}$, —OalkylC(=O)NR$^{15}$R$^{16}$, —OalkylOC(=O)R$^{18}$, —C(=S)R$^{18}$, SH, —C(=O)N($C_{1-6}$ alkyl), —N(H)S(O)(O)($C_{1-6}$ alkyl), aryl, heterocycle, $C_{1-18}$ alkylsulfone, arylsulfoxide, arylsulfonamide, aryl($C_{1-18}$)alkyloxy, aryloxy, aryl($C_{1-18}$alkyl)oxy, arylthio, aryl($C_{1-18}$)alkylthio and aryl($C_{1-18}$)alkyl, wherein aryl, heterocycle, $C_{1-18}$alkylsulfone, arylsulfoxide, arylsulfonamide, aryl($C_{1-18}$)alkyloxy, aryloxy, aryl($C_{1-18}$alkyl)oxy, arylthio, aryl($C_{1-18}$)alkylthio and aryl($C_{1-18}$)alkyl may be optionally substituted with one to three $R^{20}$;

and $R^{20}$ is selected from the group consisting of hydrogen, $C_{1-18}$ alkyl, $C_{2-18}$ alkenyl, $C_{2-18}$ alkynyl, heterocycle, $C_{1-18}$ alkoxy, $C_{1-18}$ alkylthio, $C_{1-18}$ alkylsulfoxide, $C_{1-18}$ alkylsulfone, $C_{1-18}$ halo-alkyl, $C_{2-18}$ halo-alkenyl, $C_{2-18}$ halo-alkynyl, $C_{1-18}$ halo-alkoxy, $C_{1-18}$ halo-alkylthio, $C_{3-10}$ cycloalkyl, $C_{3-10}$ cycloalkenyl, halogen, OH, CN, oxo, cyanoalkyl, —$CO_2R^{18}$, $NO_2$, —$NR^{13}R^{14}$, $C_{1-18}$ haloalkyl, C(=O)$R^{18}$, C(=S)$R^{18}$, SH, aryl, aryloxy, arylthio, arylsulfoxide, arylsulfone, arylsulfonamide, aryl($C_{1-18}$)alkyl, aryl($C_{1-18}$)alkyloxy, aryl($C_{1-18}$)alkylthio and $C_{1-18}$ hydroxyalkyl;

$R^{21}$ is hydrogen or $C_{1-6}$ alkyl;

m is an integer from 0 to 2;

and the pharmaceutically acceptable salts thereof.

24. A pharmaceutical composition comprising the compound of claim 1 or a pharmaceutically acceptable salt thereof; and at least one pharmaceutically acceptable carrier.

25. The pharmaceutical composition of claim 24, further comprising at least one additional therapeutic agent.

26. The pharmaceutical composition of claim 25, wherein said additional therapeutic agent is selected from the group consisting of interferons, ribavirin, taribavirin, rebetol, copegus, levovirin, VX-497, NS5a inhibitors, NS4b inhibitors, NS3 protease inhibitors, NS5b polymerase inhibitors, alpha-glucosidase 1 inhibitors, hepatoprotectants, non-nucleoside inhibitors of Hepatitis-C Virus HCV, and other drugs for treating Hepatitis-C Virus.

27. The pharmaceutical composition of claim 26, further comprising at least one additional therapeutic agent selected from the group consisting of pegylated rIFN-alpha 2b, pegylated rIFN-alpha 2a, rIFN-alpha 2b, rIFN-alpha 2a, interferon alpha, interferon alfacon-1, interferon alpha-n1, interferon alpha-n3, interferon-beta, interferon-omega, albinterferon alpha-2b, IFN alpha XL, BLX-883, DA-3021, glycosylated interferon alpha-2b, PEG-Infergen, PEGylated interferon lambda, and belerofon.

28. The pharmaceutical composition of claim 26, further comprising at least one additional therapeutic agent selected from the group consisting of ribavirin, and taribavirin.

29. The pharmaceutical composition of claim 26, further comprising at least one additional therapeutic agent selected from the group consisting of boceprevir, telaprevir, VX-813, TMC-435, ABT-450, BI-201335, BI-1230, MK-7009, SCH-900518, VBY-376, VX-500, GS-9256, GS-9451, BMS-790052, BMS-605339, PHX-1766, AS-101, YH-5258, YH5530, YH5531, and ITMN-191.

30. The pharmaceutical composition of claim 26, further comprising at least one additional therapeutic agent selected from the group consisting of celgosivir, Miglitol, and UT-231B.

31. The pharmaceutical composition of claim 26, further comprising at least one additional therapeutic agent selected from the group consisting of emericasan, ME-3738, GS-9450, silibilin, and MitoQ, nucleoside or nucleotide inhibitors of Hepatitis-C Virus NS5B polymerase, R1626, R7128, IDX184, IDX-102, PSI-7851, BCX-4678, valopicitabine, PS1-7977, and MK-0608.

32. The pharmaceutical composition of claim 26, further comprising at least one additional therapeutic agent selected from the group consisting of filibuvir, ABT-333, ABT-072, BI-207127, VCH-759, VCH-916, JTK-652, MK-3281, tegobuvir, VBY-708, VCH-222, A848837, ANA-598, GL60667, GL59728, A-63890, A-48773, A-48547, BC-2329, VCH-796, GSK625433, BILN-1941, XTL-2125, and tegobuvir.

33. The pharmaceutical composition of claim 26, further comprising at least one additional therapeutic agent selected from the group consisting of AZD-2836 (A-831), AZD-7295 (A-689), GS-5885, and BMS-790052.

34. The pharmaceutical composition of claim 26, further comprising at least one additional therapeutic agent selected from the group consisting of imiquimod, 852A, GS-9524, ANA-773, ANA-975, AZD-8848 (DSP-3025), PF-04878691, and SM-360320, cyclophillin inhibitors, DEBIO-025, SCY-635, NIM811, MCI-067 and Hepatitis-C Virus IRES inhibitors.

35. The pharmaceutical composition of claim 26, further comprising at least one additional therapeutic agent selected from the group consisting of BAS-100, SPI-452, PF-4194477, TMC-41629, GS-9350, GS-9585, and roxythromycin.

36. The pharmaceutical composition of claim 26, further comprising at least one additional therapeutic agent selected from the group consisting of thymosin alpha 1, nitazoxanide, BIVN-401, PYN-17, KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, FK-788, CTS-1027, SD-101, BMS-824393, MK-5172, and VX-497 (merimepodib).

37. The pharmaceutical composition according to claim 26, further comprising a nucleoside analogue, wherein said nucleoside analogue is selected from ribavirin, viramidine, levovirin, a L-nucleoside, and isatoribine.

38. The pharmaceutical composition according to claim 26, further comprising an interferon or pegylated interferon.

39. The pharmaceutical composition according to claim 38, wherein said interferon is α-interferon or pegylated interferon.

40. A method of treating Hepatitis-C Virus infection, said method comprising administering to an individual in need thereof a pharmaceutical composition which comprises a therapeutically effective amount of a compound of claim 1 or a pharmaceutically acceptable salt thereof.

* * * * *